US010073026B2

(12) United States Patent
Curry et al.

(10) Patent No.: US 10,073,026 B2
(45) Date of Patent: Sep. 11, 2018

(54) OPTICAL PARTICLE SORTER

(71) Applicant: The United States of America, as Represented by the Secretary of Commerce, Washington, DC (US)

(72) Inventors: John J. Curry, Frederick, MD (US); Zachary H. Levine, Rockville, MD (US)

(73) Assignee: THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 0 days.

(21) Appl. No.: 15/632,621

(22) Filed: Jun. 26, 2017

(65) Prior Publication Data
US 2018/0010997 A1    Jan. 11, 2018

Related U.S. Application Data

(60) Provisional application No. 62/358,264, filed on Jul. 5, 2016.

(51) Int. Cl.
*G01N 15/14* (2006.01)
*G01N 15/10* (2006.01)
*H05H 3/04* (2006.01)
*G02B 17/00* (2006.01)
*G01N 15/00* (2006.01)

(52) U.S. Cl.
CPC ..... *G01N 15/1434* (2013.01); *G01N 15/1031* (2013.01); *G01N 15/1404* (2013.01); *G02B 17/004* (2013.01); *H05H 3/04* (2013.01); *G01N 2015/0038* (2013.01); *G01N 2015/0065* (2013.01); *G01N 2015/1081* (2013.01); *G01N 2015/1087* (2013.01); *G01N 2015/149* (2013.01); *G01N 2015/1493* (2013.01)

(58) Field of Classification Search
CPC .......... G01N 15/1031; G01N 15/1404; G01N 15/1434; G01N 2015/1081; G01N 2015/0038; G01N 2015/0065; G01N 2015/1087; G01N 2015/149; G01N 2015/1493; G02B 17/004; H05H 3/04
See application file for complete search history.

(56) References Cited

U.S. PATENT DOCUMENTS 3,761,721 A * 9/1973 Altshuler ............... G01C 19/58
                                                          101/104
6,055,106 A    4/2000 Grier et al.
(Continued)

*Primary Examiner* — Eliza Osenbaugh-Stewart
(74) *Attorney, Agent, or Firm* — Office of Chief Counsel for National Institute of Standards and Technology

(57) ABSTRACT

A process for optically sorting a plurality of particles includes: providing a particle receiver; producing particles; receiving the particles by the particle receiver; receiving a light by the particle receiver; producing a standing wave optical interference pattern in an optical interference site of the particle receiver from the light; subjecting the particles to an optical gradient force from the standing wave optical interference pattern; deflecting the particles into a plurality of deflected paths to form the sorted particles from the particles; and propagating the sorted particles from the optical interference site through the deflected paths to optically sort the particles.

19 Claims, 19 Drawing Sheets

(56) References Cited

U.S. PATENT DOCUMENTS

| | | | |
|---|---|---|---|
| 2003/0008364 A1* | 1/2003 | Wang | B07C 5/34 |
| | | | 435/173.9 |
| 2014/0090979 A1* | 4/2014 | Terray | B01L 3/502761 |
| | | | 204/451 |
| 2017/0248515 A1* | 8/2017 | Duckett, Jr. | G01N 21/05 |

* cited by examiner (A)

(D)

(B) 28

(C) 28

OPTICAL PARTICLE SORTER

CROSS REFERENCE TO RELATED APPLICATIONS

This application claims the benefit of U.S. Provisional Patent Application Ser. No. 62/358,264, filed Jul. 5, 2016, the disclosure of which is incorporated herein by reference in its entirety.

STATEMENT REGARDING FEDERALLY SPONSORED RESEARCH

This invention was made with United States Government support from the National Institute of Standards and Technology, an agency of the United States Department of Commerce. The Government has certain rights in the invention.

BRIEF DESCRIPTION

Disclosed is an optical particle sorter comprising: a particle receiver comprising: a particle entrance that receives a plurality of particles; an optical entrance that receives light and that is geometrically disposed at a non-parallel angle with respect to the particle entrance; a sorted particle exit opposing the particle entrance and that communicates sorted particles from an optical interference site; and an optical interference site interposed between the particle entrance and the sorted particle exit; a first light source in optical communication with the particle receiver and that: produces a first light; and produces a standing wave optical interference pattern in the optical interference site of the particle receiver; and a particle source in fluid communication with the particle receiver and that: provides the particles; and communicates the particles to the particle receiver at an angle with respect to the first light, wherein the optical particle sorter sorts the particles into a plurality of sorted particles that exit the particle receiver at the sorted particle exit, and the sorted particles propagate along a plurality of deflected path relative to a path of propagation of the particles at the particle entrance, the deflected path of individual sorted particles along different paths based on a sorting parameter comprising a dielectric constant, a magnetic permeability, a particle volume, or a combination of one or more comprising at least one of the foregoing sorting parameters of the particles.

Also disclosed is a process for optically sorting a plurality of particles, the process comprising: providing a particle receiver; introducing the particles; receiving the particles by the particle receiver; receiving the first light by the particle receiver; producing the standing wave optical interference pattern in the optical interference site of the particle receiver from the first light; subjecting the particles to an optical gradient force from the standing wave optical interference pattern; deflecting the particles into the plurality of deflected paths to form the sorted particles from the particles; and propagating the sorted particles from the optical interference site through the deflected paths to optically sort the particles.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

Figure 1:
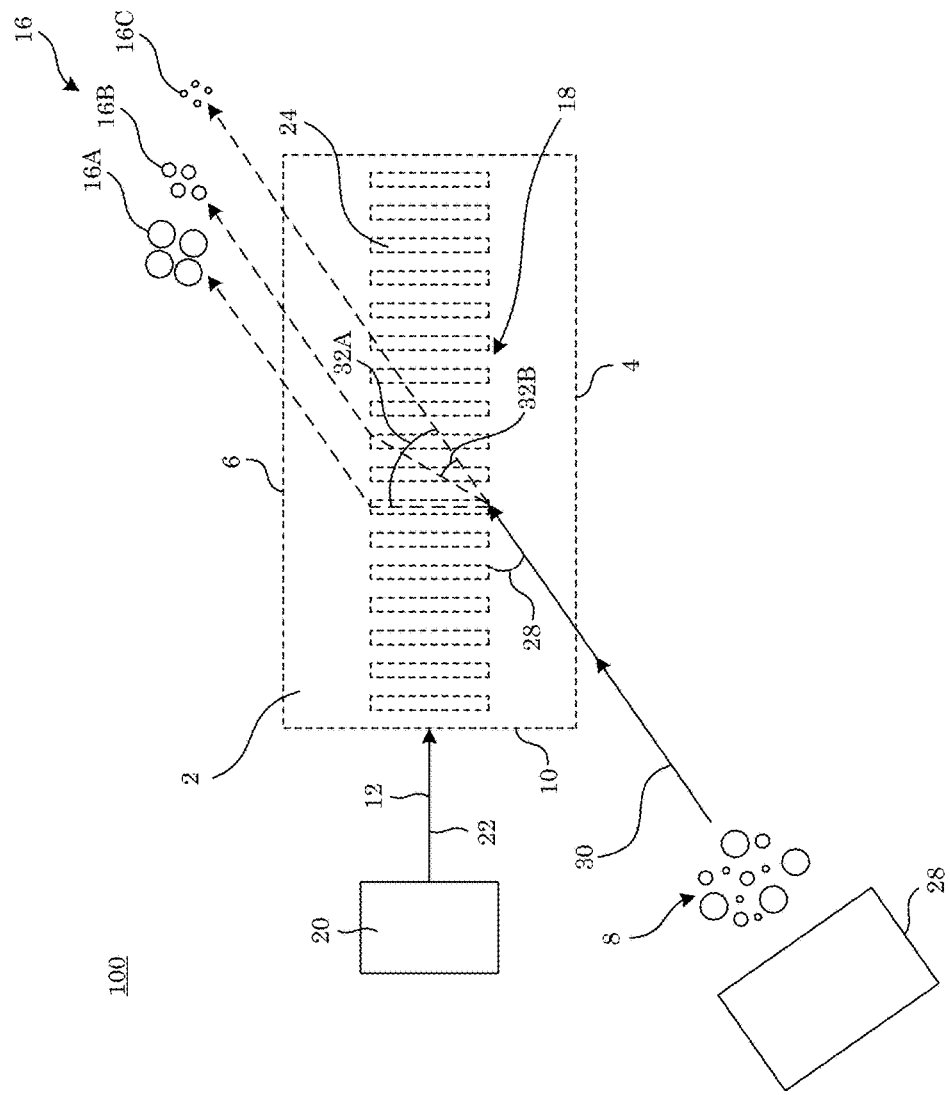
FIG. 1 shows an optical particle sorter.

In an embodiment, with reference to FIG. 1, optical particle sorter 100 includes particle receiver 2 that includes: particle entrance 4 that receives plurality of particles 8, optical entrance 10 that receives light 12 and that is geometrically disposed at a non-parallel angle with respect to particle entrance 4, a sorted particle exit opposing the particle entrance and that communicates sorted particles from an optical interference site, and optical interference site 18 interposed between particle entrance 4 and sorted particle exit 6; first light source 20 in optical communication with particle receiver 2 and that: produces first light 22 and produces standing wave optical interference pattern 24 in optical interference site 18 of particle receiver 2; and particle source 26 in fluid communication with particle receiver 2 and that: provides particles 8 and communicates particles 8 to particle receiver 2 at acute angle 28 with respect to standing wave optical interference pattern 24. Here, optical particle sorter 100 sorts particles 8 into a plurality of sorted particles 16 (e.g., 16A, 16B, 16C) that exit particle receiver 2 at sorted particle exit 6, and sorted particles 16 propagate in a plurality of deflected paths 32 (e.g., 32A, 32B) relative to path of propagation 30 of particles 8 at particle entrance 4. Deflected paths 32 of individual sorted particles (e.g., 16A, 16B, 16C, and the like) based on a sorting parameter that includes a dielectric constant, a magnetic permeability, a particle volume, or a combination thereof.

As used herein, "deflected path" refers to the path of sorted particle 16 relative to path of propagation 30 of particle 8. Path of propagation 30 occurs in an absence of optical interference field 18. The deflected path can differ in position or angle from path of propagation 30 of particles 8. Deflected paths can differ in position from 0 up to a size of particle receiver 2, more specifically from 0 to several millimeters, and more specifically from 0 to 1 mm. Deflected paths also can differ in angle from 0° up to 90°, more specifically from 0° to 45°.

Figure 2:
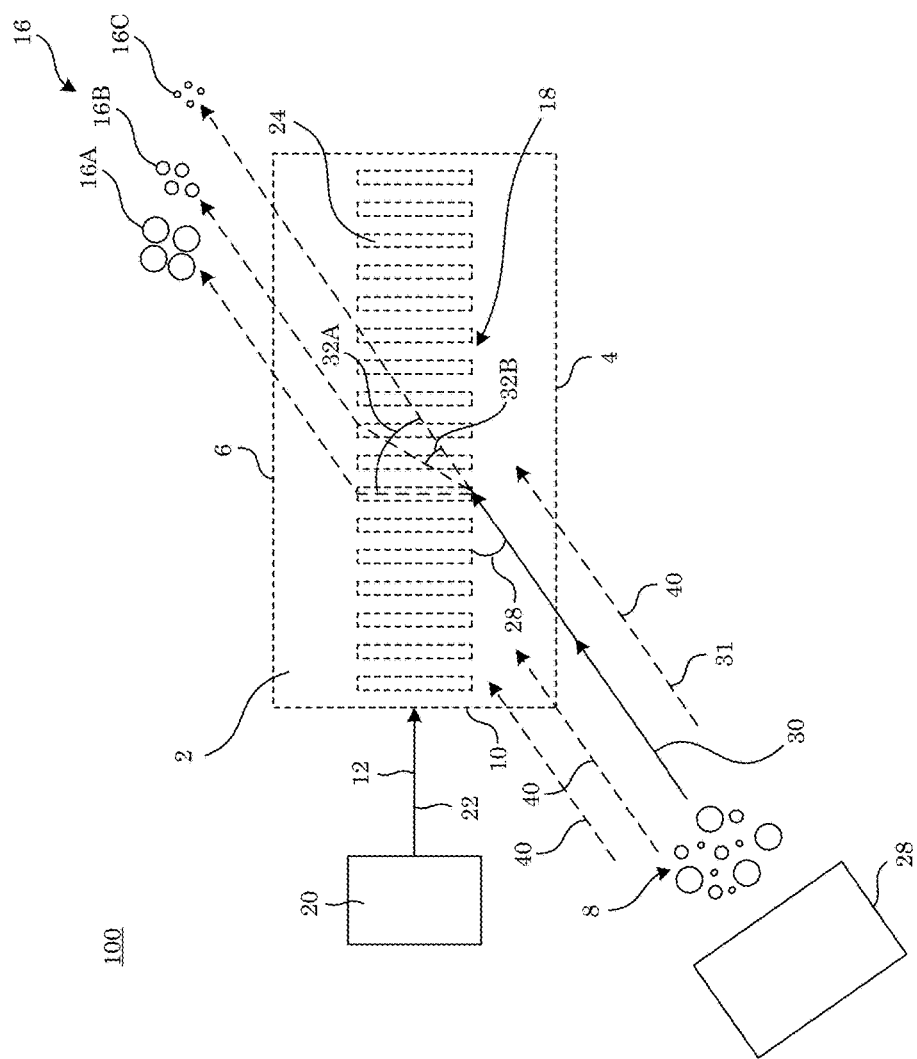
FIG. 2 shows an optical particle sorter.

In an embodiment, with reference to FIG. 2, particle source 26 provides fluid 31. Fluid 31 propagates in a plurality of laminar streamlines 40 from particle source 28 to particle receiver 2. Further, particles 8 are disposed in fluid 31 and propagate along laminar streamlines 40 of fluid 31 from particle source 28 to particle receiver 2. After deflected path 32 (e.g., 32A, 32B, and the like), sorted particles 16 propagate from standing wave optical interference pattern 24 through sorted particle exit 6 along laminar streamlines 40.

Figure 3:
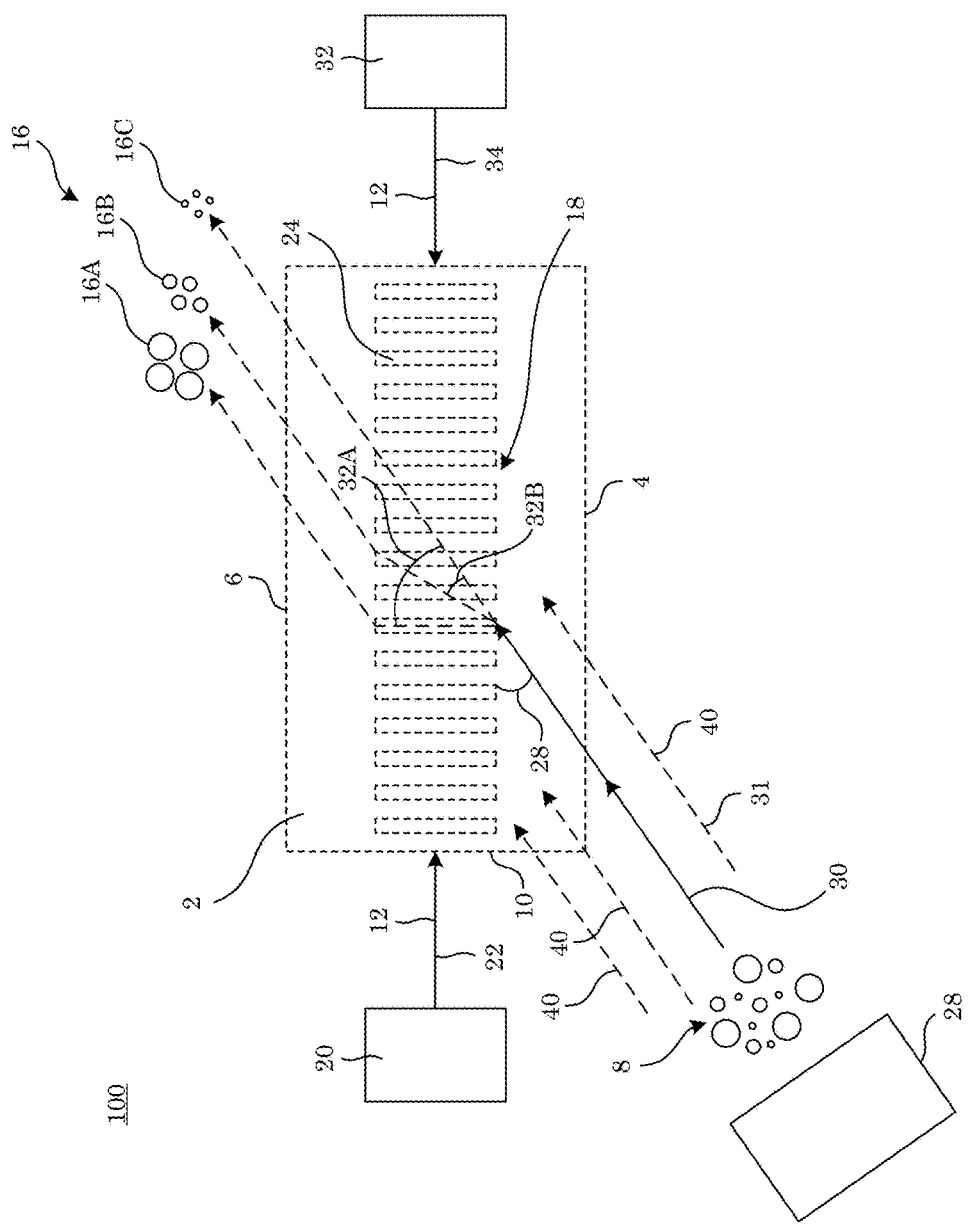
FIG. 3 shows an optical particle sorter.

In an embodiment, with reference to FIG. 3, optical particle sorter 100 includes second light source 32 in optical communication with particle receiver 2 and that produces second light 34. Second light 34 in combination with first light 22 forms standing wave optical interference pattern 24 in optical interference site 18 of particle receiver 2.

Figure 4:
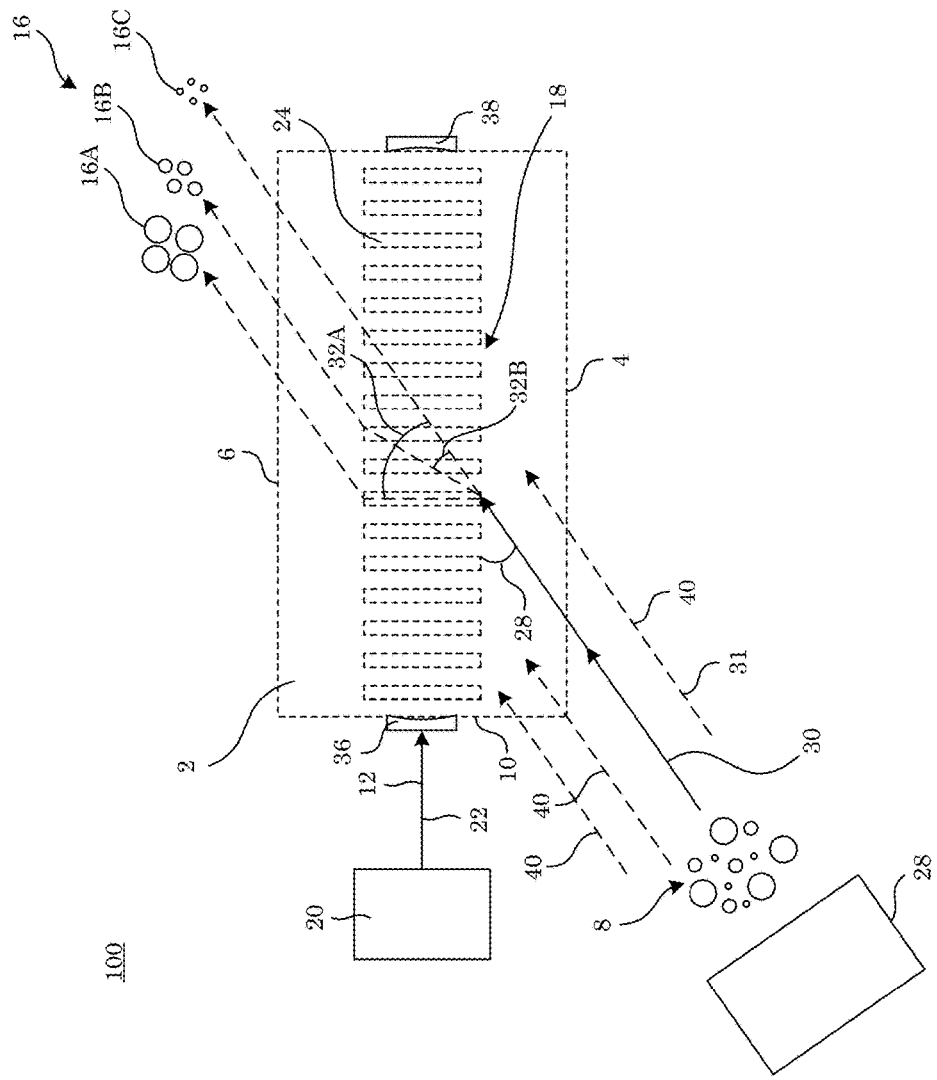
FIG. 4 shows an optical particle sorter.

In an embodiment, with reference to FIG. 4, optical particle sorter 100 includes first mirror 36 disposed at optical entrance 10 and second mirror 38 disposed opposing first mirror 36. First mirror 36 and second mirror 38 are arranged as an optical cavity. It is contemplated that the optical cavity can be, e.g., a Fabry Perot cavity.

Figure 5:
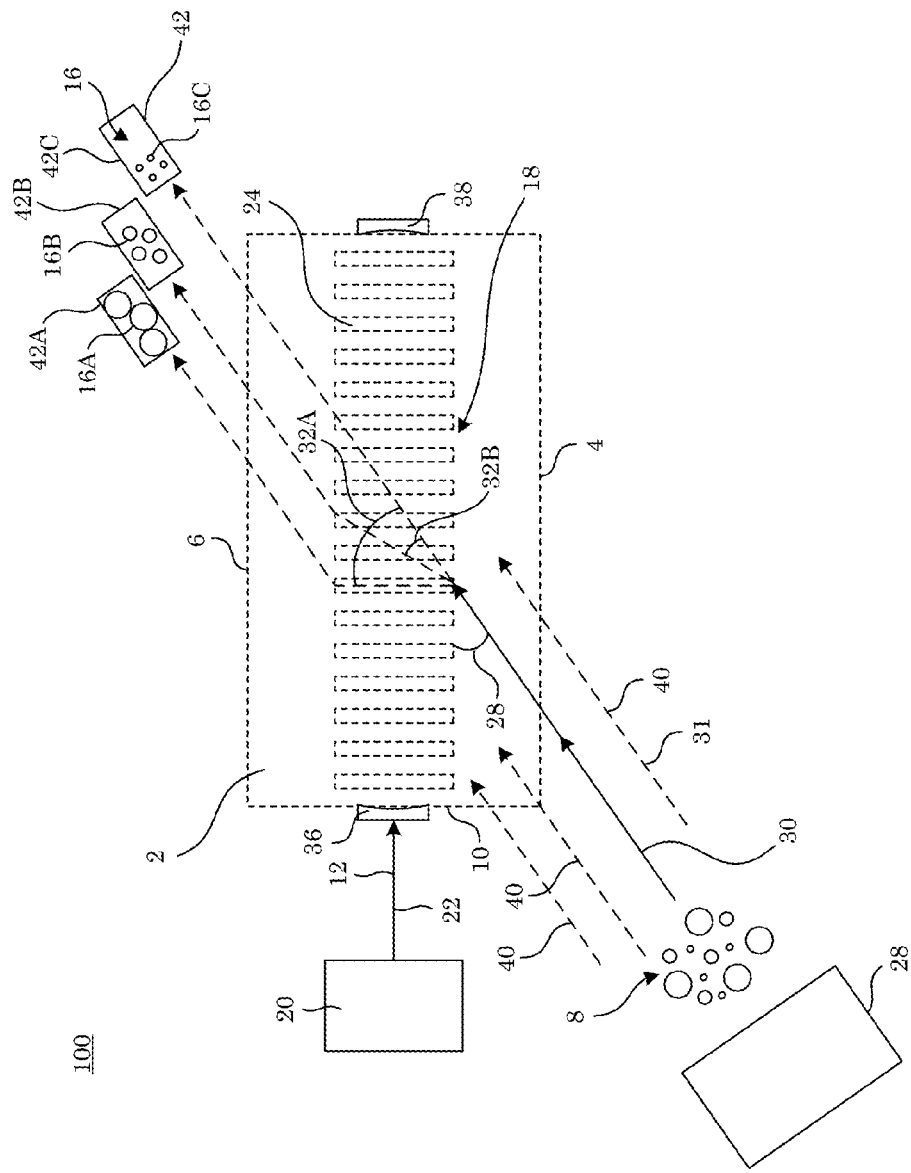
FIG. 5 shows an optical particle sorter.

According to an embodiment, with reference to FIG. 5, optical particle sorter 100 includes collector 42 disposed proximate to sorted particle exit 6 and distal to particle entrance 4 of particle receiver 2 and opposing particle source 26. Collector 42 can include a plurality of collector tubes (e.g., 42A, 42B, 42C, and the like) that receives sorted particles 16. The plurality of tubes can include first tube 42B that receives first sorted particles 16B that propagate along first deflected path 32A; and second tube 42C that receives second sorted particles that propagate along second deflected path 32B. Second deflected path 32B can be greater than first deflected path 32A. In this respect, individual second sorted particles 16C have a second particle volume, and individual first sorted particles 16B have a first particle volume that is less than the second particle volume such that sorted particles 16 that have a greater particle volume have a greater deflected path as compared to sorted particles 16 that have a smaller particle volume.

Figure 6:
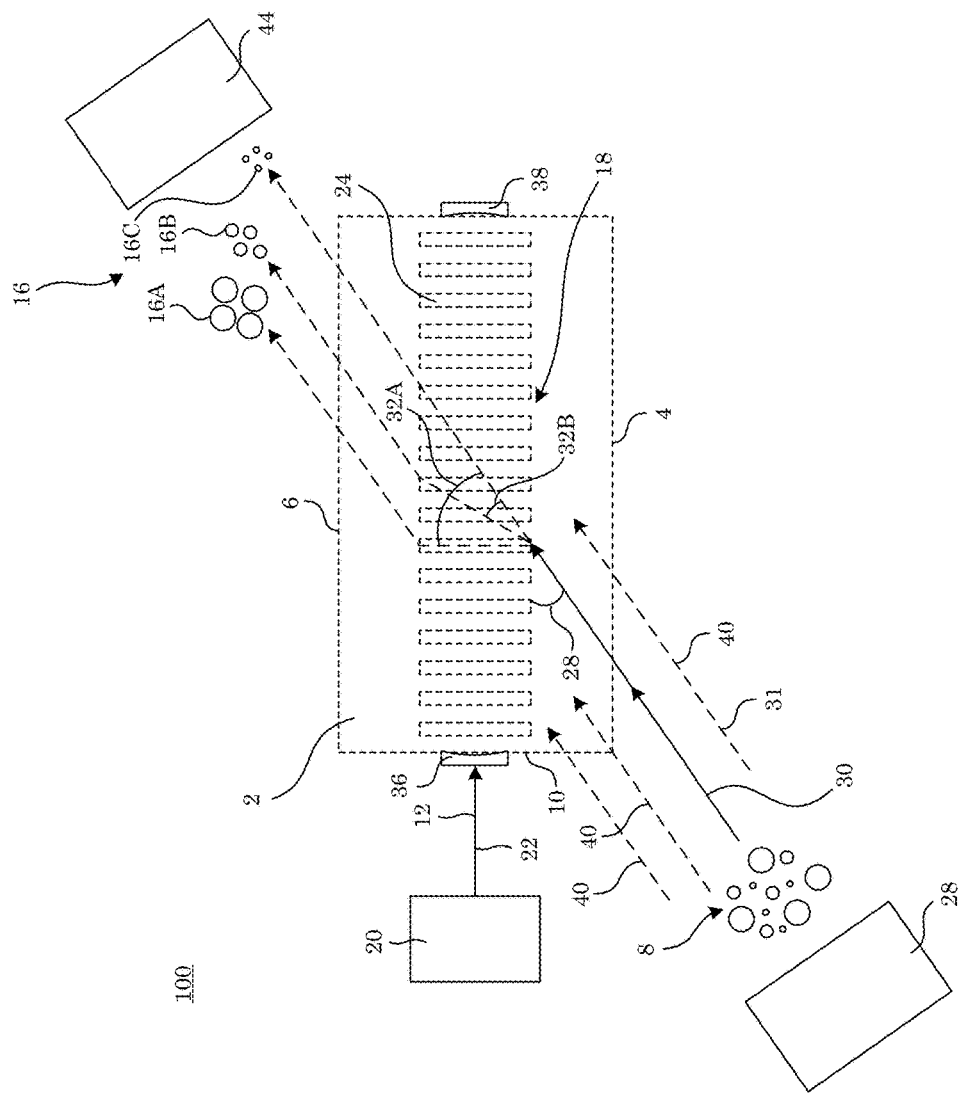
FIG. 6 shows an optical particle sorter.
Figure 7:
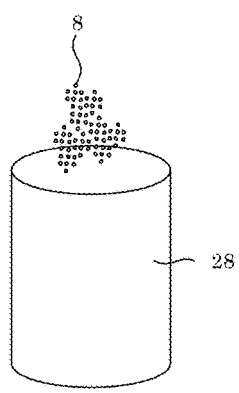
FIG. 7 shows a plurality of particle sources.
Figure 7:
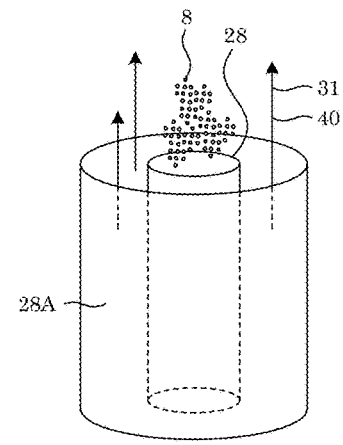
Figure 7:
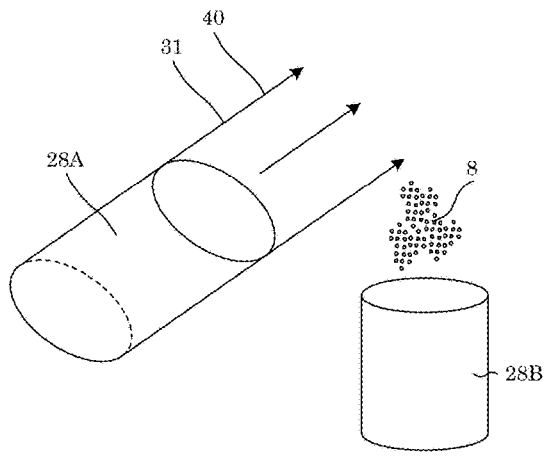
Figure 7:
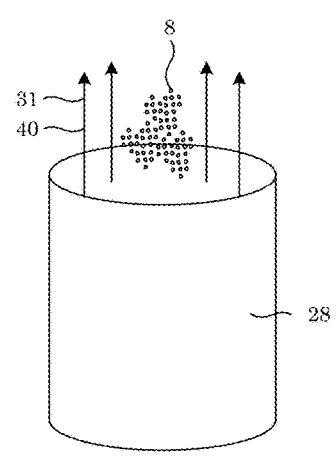

In an embodiment, with reference to FIG. 6, optical particle sorter 100 includes particle detector 44 that detects sorted particles 16.

In optical particle sorter 100, particle source 28 provides particles 8 that are to be sorted based on a dielectric constant, magnetic permeability, particle volume, or a combination thereof of particles 8. With respect to sorting particles 8, the dielectric constant, magnetic permeability, particle volume of particles 8 or collectively referred to as sorting parameters. Particle source 28 can be a microfluidic source, an effusive source, or the like. It is contemplated that particle source 28 also can provide fluid 31 laminar streamline 40 for carrying propagating particles 8 along laminar streamlines 40 to optical interference site 18 of particle receiver 2.

Particle source 28 controls particle velocity, number, and geometric arrangement. It may contain channels of various size for positioning the particles within the fluid and controlling the number density of particles within the fluid. It may contain a pump or other means for controlling fluid pressure and flow rate. It may contain the means for controlling the temperature of the fluid and other parameters. It may utilize different fluids alone or in combination in order to achieve a desired laminar streamline profile and the positioning of particles on specific laminar streamline 40. In an embodiment, particle source 28 includes a polyethylene tube whose inner diameter is at least 10 times a diameter of particles 8 to minimize accumulation of particles 8 on a wall of the tube. Particles 8 propagate in air or water. Particle source 28 also can include an adjacent fluid source. The fluid source minimizes turbulent mixing as particles 8 enter a flow field. In an embodiment, particle source 28 includes an array of tubes of that substantially similar diameter in which one tube provides particles 28 in fluid and the remainder of the tubes contain fluid. In an embodiment, particle source 28 includes a concentric tube-within-a-tube arrangement. Accordingly, particle source 28 can be made from a metal, plastic, glass, ceramic, polymer, and the like.

Particles 8 are subjected to sorting in optical interference site 18 in response to being subjected to standing wave optical interference pattern 24. Sorting of particles 8 is based upon the sorting parameter of particles 8 that can include a dielectric constant, magnetic permeability, or particle volume, wherein particles 8 with a greater dielectric constant produce sorted particles 16 that propagate with a greater deflected path than particles 8 with a smaller dielectric constant. Standing wave optical interference pattern 24 can provide sorted particles 16 with a smaller dielectric constant that propagate with a greater deflection than particles 8 with a larger dielectric constant. Particles 8 with a greater magnetic permeability produce sorted particles 16 that propagate with a greater deflected path than particles 8 with a smaller magnetic permeability. It is further contemplated that standing wave optical interference pattern 24 provide sorted particles 16 with a smaller magnetic permeability that propagate with a greater deflection than particles 8 with a larger magnetic permeability. Particles 8 with a greater particle volume produce sorted particles 16 that propagate in a greater deflected path than particles 8 with a smaller particle volume. Moreover, standing wave optical interference pattern 24 can provide sorted particles 16 with a smaller volume that propagate with a greater deflection than particles 8 with a larger volume. The dielectric constant of particles 8 is not limited to any particular range of values, real or imaginary. The magnetic permeability of particles 8 are not limited to any particular range of values. The particles 8 can be homogeneous or inhomogeneous and can be any shape. It is contemplated that the particle volume is less than 10 nanoliters (nL).

Particles 8 can include dielectric, conducting, magnetic, biological, and the like. Exemplary biological particles include a protein, amino acid, virus, bacteria, fungi, and the like. Exemplary dielectric particles include a glass, polymer, crystal, mineral, and the like. Exemplary conducting particles include gold and other metallic nano-particles and the like. Exemplary magnetic particles include particles made from ferromagnetic, paramagnetic, and diamagnetic materials and the like. In an embodiment, particles 8 include a protein molecule having a distribution of effective molecular radii from 1 nm to 100 μm.

A number density of particles 8 can be from less than 1 per cubic centimeter ($cm^{-3}$) to $10^{12}$ $cm^{-3}$, specifically from less than 1 $cm^{-3}$ to $10^6$ $cm^{-3}$, and more specifically from $10^3$ $cm^{-3}$ to $10^4$ $cm^{-3}$. A partial pressure of particles 8 can be from 0 pascals (Pa) to $10^{-2}$ Pa, specifically from 0 Pa to $10^{-8}$ Pa, and more specifically from $10^{-11}$ Pa to $10^{-10}$ Pa. A flow rate of particles can be from 10 $s^{-1}$ to $10^7$ $s^{-1}$, specifically from 100 $s^{-1}$ to $10^7$ $s^{-1}$, and more specifically $10^4$ $s^{-1}$ to $10^6$ $s^{-1}$.

Particles 8 can be disposed in fluid 31 that provides laminar streamlines 40 through which particles 8 can propagate and along which sorted particles 16 can propagate. Laminar streamlines 40 are parallel and are present from particle source 28 past sorted particle exit 6 of particle receiver 2. Exemplary fluids 31 can include air, water, ethylene glycol, salt solutions, and the like. Fluid mass densities can vary from 0 to 5 grams per cubic centimeter, more specifically from 0 grams per cubic centimeter to 2 grams per cubic centimeter, and more specifically from 0 grams per cubic centimeter to 1.1 grams per cubic centimeter.

Particles 8 disposed in fluid 31 can be formed in a beam having a transverse cross-section over any size. It is contemplated that a typical embodiment would have a cross-section from 0.1 square micrometers ($\mu m^2$) to $10^6$ square micrometers ($\mu m^2$), specifically from 0.1 $\mu m^2$ to $10^4$ $\mu m^2$, and more specifically from 100 $\mu m^2$ to 1000 $\mu m^2$.

Light sources (20, 32) independently provide light 12, e.g., first light 22 or second light 34. Exemplary light sources (20, 32) include a laser, a narrow band incoherent source, a very narrow band supercontinuum source, and the like. First light 22 and second light 34 are independently monochromatic. As used herein, "monochromatic" refers to a bandwidth sufficiently narrow such that a standing wave interference pattern of at least 10% visibility can be formed. Moreover, first light 22 and second light 34 independently can have a wavelength from 10 nm to $10^5$ nm, specifically from 200 nm to 10,600 nm, and more specifically from 248 nm to 1064 nm. First light 22 and second light 34 independently can be a continuous wave or pulsed, provided the pulse duration is sufficiently long to form a standing wave interference pattern of at least 10% visibility. A peak power of first light 22 and second light 34 independently can be from 0.01 milliwatts (mW) to 10 Watts (W), specifically from 3 mW to 1 W, and more specifically from 100 mW to 1 W. According to an embodiment, first light 22 is a continuous wave laser light having an average power of 100 mW. An exemplary longitudinal mode for first light source and second light source is a fundamental Gaussian mode.

Standing wave optical interference pattern 24 formed by first light 22 alone or in combination with second light 34 can include a plurality of fringes and nodes that provide an optical force gradient to particles 8 that traverse standing wave optical interference pattern 24 at optical interference site 18. Standing wave optical interference pattern 24 can be formed by reflection of first light 22 in particle receiver 2 such that the incident first light 22 optically interferes with reflected first light 22 in optical interference site 18 to form standing wave optical interference pattern 24. Standing wave optical interference pattern 24 can be formed by combination of first light 22 and second light 34 in particle receiver 2 such that the two combine to form an optical interference of arbitrary pattern, shape, and size. In such case, first light 22 and second light 34 must have a controlled phase relationship.

Particle Receiver 2 receives particles 8 from particle source 20 and particle entrance 4, first light 22 from first light source 20 at optical entrance 10, second light 34 from second light source 32, or a combination thereof. Particle receiver 2 can be a physical space at an intersection of particles from particle source 28 and first light 22 from first light source 20. It is contemplated that particle receiver 2 can be free space or can include a container such as a chamber bounded by walls. In an embodiment, particle receiver 2 includes the container such that particle entrance 4 is in fluid communication with particle source 28 through a fluid flow line, and optical entrance 10 includes an optical window to receive first light 22 as light 12.

A pressure of particle receiver 2 can be any pressure effective for sorting particles 8 into sorted particles 16 via deflection through deflected path 32. Moreover, a temperature of particle receiver 2 can be any temperature effective for sorting particles 8 into sorted particles 16 via deflection through deflected path 32. In an embodiment, particle receiver 2 is at standard temperature and pressure. In an embodiment, particle receiver 2 is a vacuum chamber at a pressure less than 0.1 Pa.

Particle receiver 2 can include the cavity, wherein first mirror 36 is disposed at optical entrance 10 and second mirror 38 is disposed opposing first mirror 36. Here, first light 22 is communicated from first light source 20 through first mirror 36, through optical interference site 18, reflected by second mirror 38, again communicated through optical interference site 18, producing standing wave optical interference pattern 24 in optical interference site 18, and reflected from first mirror 36 back toward second mirror 38. First mirror 36 and second mirror 38 independently can reflect 99% or more of first light incident upon them. Independently, they may be plane mirrors or focusing mirrors. One of the two may be a defocusing mirror.

Collector 42 can be disposed proximate to sorted particle exit 6 to receive sorted particles 16 from particle receiver 2. Here, collector tubes can be spaced apart to selectively receive sorted particles 16 binned by sorting parameter. Collector tubes (42A, 42B, 42C, and the like) can be as small as the largest particles to be sorted and as large as the particle receiver. Exemplary collector tubes have diameters at least 10 times the particle size, but much smaller than the particle receiver. They may be placed next to each other as an integrated array of tubes. The tubes may be circular in cross section, square, rectangular, or any other shape. tube lengths in the range of 1 mm to 10 m can be envisioned. Tubes may be pumped to ensure a continuous process. As an alternative, the particles can be sorted into small boxes with openings described above which are swapped out when full. A number (e.g., 1, 2, . . . , 10, . . . , 1000, and the like) of collector tubes 42 can be selected based on a number of bins of sorting parameters desired. Exemplary materials for collector tubes 42 include a metal, glass, polymer, ceramic, and the like. Both ends of collector tubes 42 can be open and that collector tubes 42 transmit sorted particles 16 therethrough, or collector tubes 42 can be a blind tube such that collector tubes 42 capture sorted particles 16 in an absence of further transmission of sorted particles 16.

Particle detector 44 can be disposed proximate to sorted particle exit 6 to receive sorted particles 16 from particle receiver 2. Detector 44 can detector particles based on optical probing and scattered light, physical bins or exit tubes, and the like. Exemplary detectors 44 include a laser at a wavelength other than that of the interference field which can be scattered off of the sorted particles, an array of tubes with a diameter of 10 times the particle diameter with a moderate pressure drop to gently suck in both particles and fluid, and the like.

In an embodiment, a process for making optical particle sorter 100 includes generating particles, optionally generating a background fluid undergoing laminar flow to carry the particles, introducing the particles into the fluid with a minimum of turbulent mixing, setting up a standing wave interference pattern, passing the particles across the standing wave interference pattern possibly by entraining the particles in a fluid, passing the particles away from the optical interaction region, and detecting the particles optically, separating the particles physically, or capturing the particles in containers.

Optical particle sorter 100 has numerous beneficial uses, including optically sorting a plurality of particles. In an embodiment, a process for optically sorting a plurality of particles 8 includes: providing particle receiver 2; producing particles 8; receiving particles 8 by particle receiver 2; receiving first light 22 by particle receiver 2; producing standing wave optical interference pattern 24 in optical interference site 18 of particle receiver 2 from first light 22; subjecting particles 8 to an optical gradient force from standing wave optical interference pattern 24; deflecting particles 8 into the plurality of deflected paths 32 to form sorted particles 16 from particles 8; and propagating sorted particles 16 from optical interference site 18 through deflected paths 32 to optically sort particles 8.

In an embodiment, the process for optically sorting particles 8 further includes providing second light 34 from second light source 32 in optical communication with particle receiver 2; and forming standing wave optical interference pattern 24 by combining first light 22 and second light 34.

In an embodiment, the process for optically sorting particles 8 further includes: provides fluid 31 from particle source 28; and propagating fluid 31 in a plurality of laminar streamlines 40 from particle source 28 to particle receiver 2. Here, particles 8 can be disposed in fluid 31 and propagate along laminar streamlines 40 of fluid 31 from particle source 28 to particle receiver 2.

In an embodiment, the process for optically sorting particles 8 further includes: collecting sorted particles 16 by collector 42 that includes a plurality of tubes disposed proximate to sorted particle exit 6 and distal to particle entrance 4.

In the process for optically sorting particles, producing particles 8 includes creating a narrow stream of particles by means of a tube or by means of hydrodynamic focusing, controlling the rate of flow of particles by means of a pump or pumps, and controlling the density of particles by the ratio of particles to fluid.

In the process for optically sorting particles, receiving particles 8 by particle receiver 2 includes manipulating the fluid flow such that the particles enter the receiver on a flowline, with the required spatial distribution and velocity.

In the process for optically sorting particles, receiving first light 22 by particle receiver 2 passing the light through vacuum or a clear fluid such as air then passing the light through an optical window if the boundary of the particle receiver 2 is physically embodied.

In the process for optically sorting particles, producing standing wave optical interference pattern 24 in optical interference site 18 of particle receiver 2 from first light 22 includes controlling the phase and focal properties of the first light in order to obtain a standing wave interference pattern of the desired radial dependence and intensity. In the case of utilizing both first light 22 and second light 34, aligning the first light 22 with second light 34 travelling in the opposite direction or a counterpropagating beam derived from the first light and a mirror or set of mirrors while maintain a coherence length in the sources sufficient to maintain the interference patter, typically a minimum coherence length of 1 m.

In the process for optically sorting particles, subjecting particles 8 to an optical gradient force from standing wave optical interference pattern 24 includes passing the particles into the optical interference field at a sufficiently low velocity so that the optical forces can lead to significant deflected paths, but a sufficiently high velocity such that diffusion is not an overwhelming effect.

In the process for optically sorting particles, deflecting particles 8 into the plurality of deflections 32 to form sorted particles 16 from particles 8 includes passing the particles across the interference field, maintaining laminar flow in the background fluid (if present), moving the particles sufficiently quickly across the device to prevent the particles from undergoing excessive diffusion.

In the process for optically sorting particles, propagating sorted particles 16 from optical interference site 18 through deflections 32 to optically sort particles 8 includes passing the particles away from the interference field, maintaining laminar flow in the background fluid (if present), moving the particles sufficiently quickly across the device to prevent the particles from undergoing excessive diffusion, allowing the integrated deflections along the path to yield an offset which is the physical embodiment of sorting outside of the particle receiver 2.

In the process for optically sorting particles, providing second light 34 from second light source 32 in optical communication with particle receiver 2 includes passing the light through vacuum or a clear fluid, passing the light through an optical window if there is a physical boundary to the particle receiver 2.

In the process for optically sorting particles, forming standing wave optical interference pattern 24 by combining first light 22 and second light 34 includes aligning the second light into a counterpropagating direction relative to that of first light 22 and locking the phases of the source of first light 22 and second light 34.

In the process for optically sorting particles, providing fluid 31 from particle source 28 includes ensuring that the fluid moves in laminar flow at a constant rate, ensuring that the particles enter the fluid with a minimum of turbulent mixing.

In the process for optically sorting particles, propagating fluid 31 in a plurality of laminar streamlines 40 from particle source 28 to particle receiver 2 includes selecting a fluid which interacts with the optical field uniformly, usually by having the interaction be very small and hence uniformly nearly zero, and ensuring that the fluid maintains laminar flow throughout the device.

In the process for optically sorting particles, collecting sorted particles 16 by collector 42 includes passing the particles into tubes which lead the particles to an exit in a continuous manner or collecting that particles in small bins with a filter which allows the passage of the fluid while trapping the particles by the filter.

After producing sorted particles 42 (e.g., 42A, 42B, 42C, and the like), sorted particles 42 can be used in analysis of a larger sample, can be used to produce particles of desired characteristics for use in research and manufacturing, can be eliminated from a larger sample as an unwanted byproduct, for example, the sorting and removal of aggregated protein particles in a manufactured biologic pharmaceutical.

Optical particle sorter 100 has numerous advantageous and beneficial properties. In an aspect, optical particle sorter 100 sorts a continuous stream of particles; produces a high throughput of sorted particles; eliminates any physical contact of particles with surfaces in the sorting region; gives a continuous dispersion of particles in the selected sorting parameter; or sorts with extremely high resolution or sorts across a large dynamic range.

The articles and processes herein are illustrated further by the following Example, which is non-limiting.

EXAMPLE

Continuous-feed optical sorting of aerosol particles.

This Examples describes sorting, by size, spherical particles of order 100 nm radius. The scheme we analyze includes a heterogeneous stream of spherical particles flowing at an oblique angle across an optical Gaussian mode standing wave. Sorting is achieved by the combined spatial and size dependencies of the optical force. Particles of all sizes enter the flow at a point, but exit at different locations depending on size. Exiting particles may be detected optically or separated for further processing. The scheme has the advantages of accommodating a high throughput, producing a continuous stream of continuously dispersed particles, and exhibiting excellent size resolution. Monte Carlo simulations of particle trajectories through the optical field under the influence of convective air flow are described. A method for deriving effective velocities and diffusion constants from the Fokker-Planck equation are described. With an optical wavelength of 1064 nm, polystyrene particles with radii in the neighborhood of 275 nm, for which the optical force vanishes, may be sorted with a resolution below 1 nm.

Conventional optical tweezers use a high numerical aperture (NA) microscope objective to focus a laser beam to a diffraction-limited spot. The strong spatial gradients in optical intensity produce trapping in three dimensions. Strong intensity gradients can also be produced by near-field structures, interference fringes, and optical fibers. Some of these techniques also utilize high NA optics. The trapping volume can be relatively small (<1 µm) and located relatively close to a microscope objective.

Optical forces can solve measurement challenges involved with aerosol particles. It is possible to manipulate and measure aerosol particles without altering or perturbing the particles as involved in diffusion mobility analysis or in collection by mechanical filters. Measurement of aerosol particles arises in such disparate fields as climate science, nano-particle manufacturing, homeland security, healthcare, and forensics.

A desirable functional capability for particle measurement is sorting, including size being a sorting parameter. Sorting makes it possible to measure particle size distributions, to manufacture mono-disperse particles, and to detect the presence of a specific type of particle.

High throughput is desirable in sorting particles. High throughput can be facilitated by parallel processing, which involves a larger working volume than a conventional trapping volume of optical tweezers. Here, we describe a scheme for optically sorting airborne nanoparticles. The optical sorting has the advantages of (1) utilizing a simple, low NA optical system with high particle throughput, (2) producing a continuous stream of continuously dispersed particles, and (3) exhibiting a size resolution better than 1 nm.

We have explored the performance of the sorting scheme using numerical simulations of optical and collisional forces. The reliability of the numerical results is enhanced by our use of two separate algorithms. One of the algorithms is a Monte Carlo solution to the equations of motion for individual particle trajectories through 6-dimensional phase space. The other approach uses the Fokker-Planck equation to determine effective velocities and diffusion constants obtained by averaging over the interference fringes of the optical field; these functions of optical intensity are then used to integrate the equations of motion over the large-scale structure of the field.

An input to the simulations is the force of a standing wave (wavelength $\lambda_0$) on a particle of arbitrary radius a. We derive this force from first principles. It reproduces existing expressions for the force in the Rayleigh regime $a \ll \lambda_0$.

This Example is directed to particles in gas but is applicable to particles in liquids. In water, for example, the drag force is nearly two orders of magnitude larger, while Brownian motion is nearly one order of magnitude smaller. The former can be accommodated by adjusting controllable parameters. The latter is generally beneficial.

Figure 8:
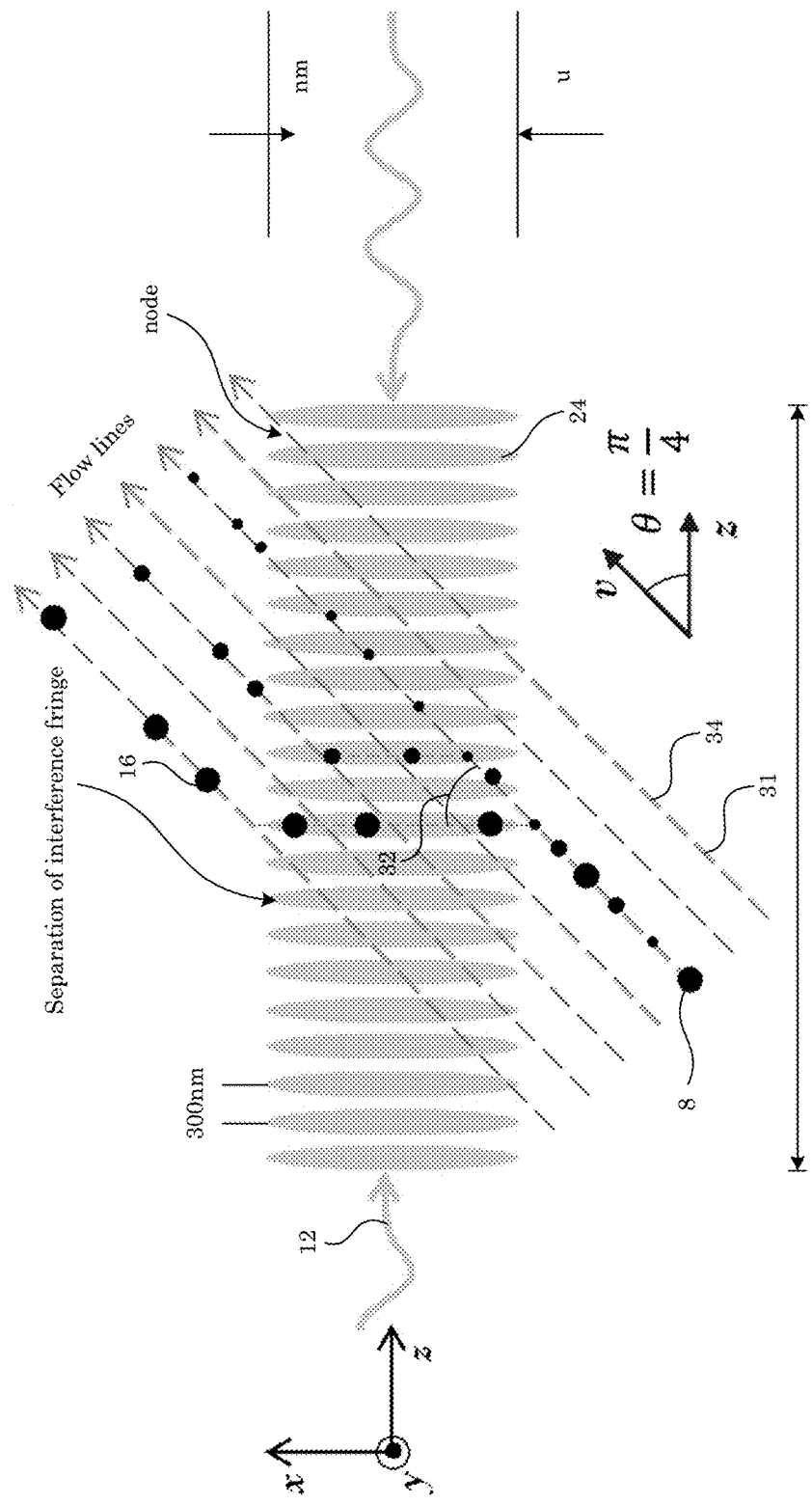
FIG. 8 shows sorting particles by size that includes a narrow stream of particles propagating across a standing wave optical interference pattern at an acute angle.

The optical sorter sorted spherical particles by size. The optical sorter configuration is shown in FIG. 8 and included a heterogeneous stream of aerosol particles, entrained in a global laminar air flow, moving across a Gaussian-mode standing wave at an oblique angle. A Cartesian coordinate system x, y, z (See FIG. 8) is chosen in which the z-axis coincides with the optical axis and the air flows parallel to the x-z plane. Particles of all sizes enter the optical field in a narrow input stream, but are physically separated by their interaction with the field. They exit the field at different locations depending on their size.

In absence of an optical field, the particle stream flows in a straight line across the optical axis. A standing wave optical field presents a sinusoidal force directed along the optical axis. The large gradients in a standing wave make this force comparable in magnitude to that seen in conventional optical tweezers. It is sufficient to impede long-range motion of particles in z but does not affect motion in x and y. Sorting of particles arises from the size-dependence of the optical force combined with the dependence on distance from the optical axis. In the Rayleigh regime, some particles are small enough that they are practically unaffected by the optical field and flow nearly undiverted in a straight line across the optical axis. Larger particles will be diverted into a purely x-directed motion when they get close to the optical axis where the optical field is largest. Particles of even larger size are diverted at lower field strengths that occur farther from the optical axis. Thus, particles of different sizes are physically separated from each other. The separation increases, by the same amount, as the particles exit the optical field and begin to flow, again, along laminar streamlines. The net result is a continuous dispersion of particle sizes along z. Particle size distributions may then be measured in situ, or the different sizes may be separated permanently for retention or subsequent analysis, depending on the application.

This problem involves an optical force, a drag force from the air, and diffusion of particles due to random collisions with air molecules. The latter makes the problem three-dimensional, but for the conditions we explore, diffusion in the y-dimension is not so important.

With regard to an optical force on a dielectric sphere in a standing wave, expressions for the force on a spherical particle in terms of the Mie coefficients are known, and we consider the force exerted on a spherical dielectric particle of arbitrary radius by a standing wave.

The force exerted by an arbitrary electromagnetic field on an arbitrary object can be obtained by generalizing the point charge in the Lorentz force equation to a charge density and a current density and then integrating over the object volume. Gauss's law and Ampere's law make it possible to describe the charge and current densities in terms of material properties, i.e., dielectric permittivity e and magnetic permeability µ. The Maxwell-Faraday equation and Gauss's law for magnetism can then be used to obtain the electromagnetic force on an object according to Eq. (1):

$$\langle F \rangle = \int \nabla \cdot \langle \overline{T} \rangle dV - \frac{1}{c^2} \int \frac{\partial \langle S \rangle}{\partial t} dV \qquad (1)$$

in terms of the divergence of the Maxwell stress tensor of Eq. 2:

$$T \equiv \left(\varepsilon_0 EE + \frac{1}{\mu_0}BB\right) - \frac{1}{2}\left(\varepsilon_0|E|^2 + \frac{1}{\mu_0}|B|^2\right)\bar{I} \quad (2)$$

and the time rate-of-change of the Poynting vector S. The integral is over the volume of the object. The brackets ⟨ ⟩ indicate a time-average over optical frequencies, $\bar{I}$ is the identity matrix and E and B are the electric and magnetic field vectors, respectively. These fields must be obtained from the incident fields by applying the appropriate boundary conditions at the object surface. EE and BB are dyadics. We will only consider situations in which the electromagnetic field has a single optical frequency time-dependence, so the last term in Eq. (1) does not contribute to the time-averaged force.

In a material medium, the electromagnetic stress tensor must be accompanied by corresponding terms describing the momentum carried by the medium. In the case of a particle in vacuum, such terms vanish. We will proceed from this point as if the electromagnetic properties of air are identical to those in vacuum.

Considering a spherical particle, it is easier to evaluate the force when the volume integral is converted to a surface integral using the Divergence Theorem of Eq. (3):

$$\langle F \rangle = \oint \langle \bar{T} \rangle \cdot dA \quad (3)$$

where the surface of integration must be outside the particle, i.e., the fields must be those external to the particle. Both incident and scattered fields are included in E and B.

We are concerned with the force generated by a low numerical aperture standing wave, so we consider an infinite plane standing wave with electric field $$E(x, y, z, t) = \hat{x}E_0 \sum_{\pm} \cos(\omega t \pm k_0 z), \quad (4)$$

where $\omega/(2\pi)$ is the optical frequency, $k_0 = 2\pi/\lambda_0$ is the wave number of the optical field, $\lambda_0$ is the free-space wavelength, and z is the coordinate along which the waves propagate. This field creates a time-averaged intensity $$\langle I(z) \rangle = 2I_0(1 + \cos 2k_0 z), \quad (5)$$

where $$I_0 = \sqrt{\frac{\varepsilon_0}{\mu_0}} \frac{|E_0|^2}{2} \quad (6)$$

is the power per unit area in each plane wave.

We have obtained the force on a spherical particle of arbitrary radius in a plane standing wave by numerically evaluating Eq. 3. The validity of the results is ensured by our use of two different approaches to the numerical evaluation, which were implemented in isolation. In one approach, the incident and scattered fields were derived analytically (in terms of Bessel and Hankel functions) and then evaluated numerically at the surface of the particle. In the second approach, the fields inside the particle were derived analytically (in terms of Bessel functions only). The fields on the external surface of the particle were then obtained from the continuity of the tangential components of the electric and magnetic fields and the continuity of the normal components of the electric displacement and magnetic induction. The force obtained from numerical evaluation of these fields is in agreement everywhere with the force obtained by the first approach.

The five-term expansion of Eq. 3 about $k_0 a = 0$ provided by Eq. (7)

$$\langle F \rangle \approx \hat{z}\frac{4\pi}{105ck_0^2}I_0\sin(2k_0 z) \quad (7)$$

$$\sum_{\ell=1}^{5}[c_{1\ell}\mathrm{Im}(a_\ell - b_\ell) + c_{2\ell}\mathrm{Im}(a_{\ell-1}a_\ell^* - b_{\ell-1}b_\ell^*) + c_{3\ell}\mathrm{Im}(a_\ell b_\ell^*)]$$

is an excellent analytic approximation to the time-averaged force of a standing wave on a spherical particle in vacuum for the range of parameters we consider. The Mie coefficients $a_l$ and $b_l$ are given in the literature by Zangwill. Values for the coefficients $c_{il}$ are given in Table 1. The first term in Eq. (7) represents a product of the incident electric field and the scattered field, whereas the following two terms represent the product of the scattered field with itself.

TABLE 1

| l | $c_{1l}$ | $c_{2l}$ | $c_{3l}$ |
|---|---|---|---|
| 1 | 630 | 0 | 630 |
| 2 | −1050 | 630 | −350 |
| 3 | 1470 | −1120 | 245 |
| 4 | −1890 | 1575 | −189 |
| 5 | 2310 | −2016 | 154 |

For $k_0 a \to 0$, Eq. (7) reduces to $$\langle F_z \rangle = -\frac{8\pi k_0 a^3 I_0}{c}\frac{n_p^2 - 1}{n_p^2 + 2}\sin(2k_0 z), \quad (8)$$

which agrees with the expression for the gradient force in the Rayleigh limit when the optical field is a plane standing wave. The Clausius-Mossotti term (n2p−1)/(n2p+2)(np2−1)/(np2+2), frequently introduced in the literature by an ad hoc argument involving scooped spheres and dipoles, is seen here to originate naturally as the lowest order consequence of the electromagnetic boundary conditions at the surface of a dielectric sphere, in particular, through the Mie coefficient $b_1$.

Figure 9:
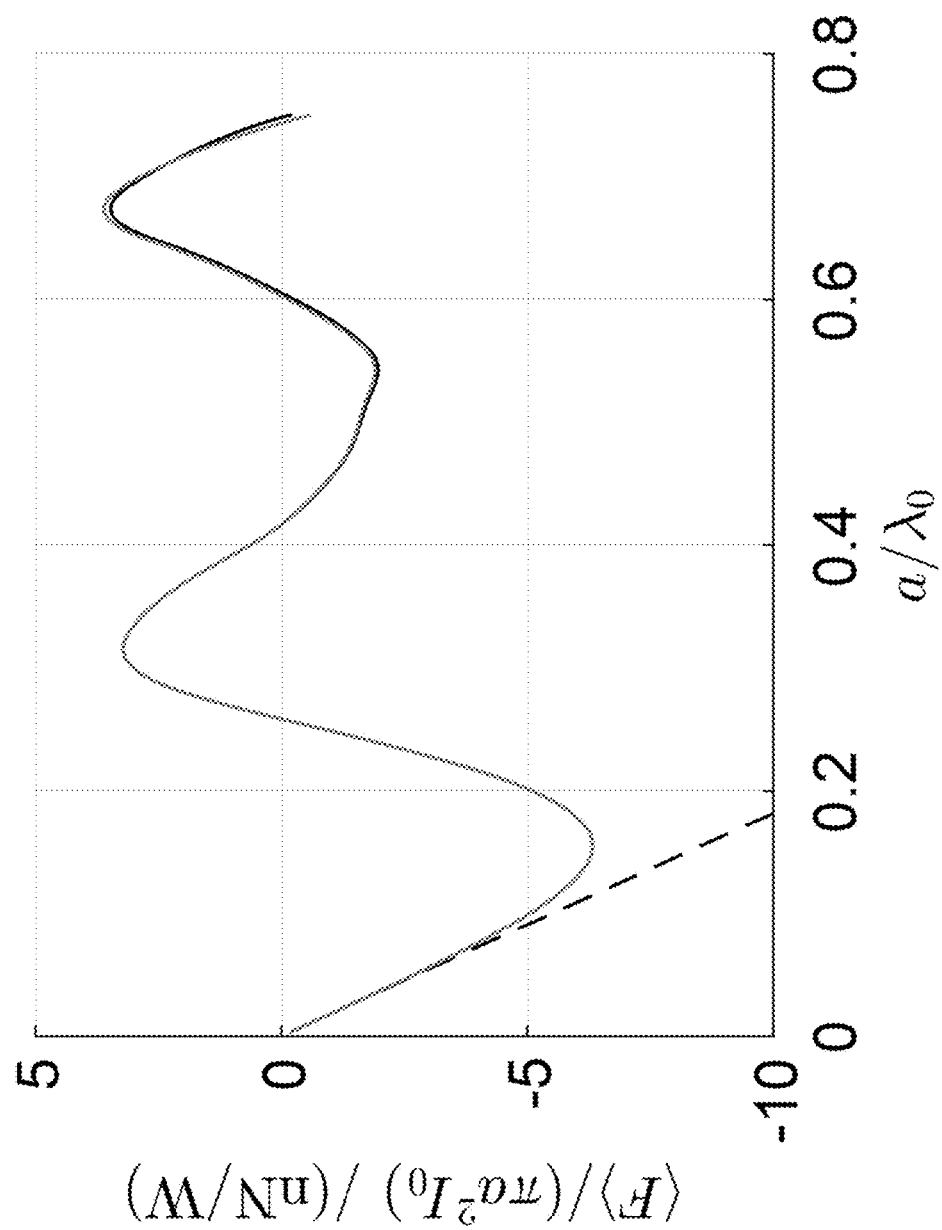
FIG. 9 shows a graph of force per unit of optical power versus $a/\lambda_0$.

FIG. 9 compares three different expressions for the force on a spherical dielectric particle in a standing wave: the Rayleigh expression of Eq. (8), our analytic approximation Eq. (7), and the essentially exact force obtained from evaluating formula (3) to order l=30. The force is normalized by the factor $I_0 \pi a^2$, so that the plotted functions give the force per unit of optical power incident on the sphere. The force is everywhere proportional to $\sin 2k_0 z$, with $z = \lambda_0/8$ in the figure.

The Rayleigh expression diverges qualitatively from the exact solution for $a/\lambda_0 > 0.1$, while our approximate expression is in excellent agreement for the range of $a/\lambda_0$ shown in FIG. 9, including the irregular behavior. The force vanishes for particles of certain sizes. This is to be expected when the particle size has a certain relationship to an integral number of fringes of the optical field. It is perhaps surprising that the force changes sign even though the particle center remains fixed relative to the standing wave. When the force is negative, a particle with index of refraction greater than that of the medium prefers to sit in the intensity maximum. When the force is positive, the particle prefers to have its center in the intensity minimum. For our scheme, this small shift of position has no practical significance.

The vanishing of the optical force for certain discrete radii is potentially useful for tying particle sizes to an SI length standard because the radii at which the zero-crossings occur are proportional to the optical wavelength. The latter can be measured accurately to high precision. There is also a dependence on the particle index of refraction, but this parameter can also be measured independently.

The preceding results have been derived for a plane standing wave, but we can use them directly in simulating the force from a Gaussian $TEM_{00}$ mode standing wave because the forces arising from the finite radial extent of the beam are small enough to be ignored relative to the axial force from the interference fringes. Considering a Rayleigh length much greater than the spatial extent of the sorter, the $TEM_{00}$ mode looks like a collimated beam and the force can be approximated by $$\langle F_z \rangle = \langle F_z^{(0)} \rangle I_0 \sin 2k_0 z e^{-\frac{2(x^2+y^2)}{w_0^2}}, \quad (9)$$

where $\langle F(0)z \rangle \langle Fz(0) \rangle$ is the force per unit irradiance exerted by a plane standing wave when the particle's position is such that $2k_0 z = n/2$, $I_0$ is the intensity of each plane wave at the waist, and $w_0$ is the $e^{-2}$ intensity radius. The Rayleigh length corresponding to a given beam waist radius is $$z_R = \frac{\pi w_0^2}{\lambda_0}. \quad (10)$$

With regard to collisional forces, we describe the general theory of the transport of spherical particles in a fluid, then discuss two models for calculating particle trajectories under the combined influences of optical forces and collisional forces. One model solves the three-dimensional equations of motion numerically, using a Monte Carlo algorithm to account for the random nature of collisional forces. Here, collisions are incorporated as random changes in particle velocity, so the six-dimensional phase-space probability distribution is utilized. A second model greatly simplifies the picture of collisions, by assuming that the velocity-space distribution equilibrates with the background gas in a time much shorter than the time required for a particle to move a significant distance. This and the quasi-1D symmetry of the optical field allows the particle dynamics along the optical axis to be described with a one-dimensional spatial probability distribution function. Effective velocities and diffusion coefficients describe the modification of trajectories produced by the one-dimensional fringes of a given magnitude. The particle trajectories perpendicular to the optical axis are described by integrating the equations of motion across the radially-inhomogeneous optical field using the effective fluid parameters appropriate to each location.

The use of two different numerical approaches adds confidence to the correctness of results. The second method is quite a bit faster computationally. We begin this section with background common to both models, Section 5 discusses the Monte Carlo specific issues, and Section 6 discusses the use of effective velocities and diffusion constants.

The trajectory of a particle under the influence of collisions with air molecules is stochastic and can be described by the time evolution of the single-particle phase-space probability distribution function f such that $$f(r, v, t | r_i, v_i, t_i) d^3 r d^3 v \quad (11)$$

gives the probability that a particle will, at time t, be found within the volume $d^3 r$ about r and within the velocity range $d^3 v$ about v after having an initial position $r_i$ and initial velocity $v_i$ at time $t_i$, hereafter taken to be 0. The probability distribution function is normalized such that integration over all final positions and velocities yields a probability of one. The time evolution of f is described by the Boltzmann equation $$\frac{df}{dt} = v \cdot \nabla_f + \nabla_v \cdot \frac{F(r,t)}{m_p} f + \left(\frac{df}{dt}\right)_c, \quad (12)$$

in which $\nabla_v$ is the gradient in velocity-space, F represents the optical forces on the particle, $m_p$ is the particle mass, and (dfdt)c(dfdt)c represents the stochastic forces of collisions between the particle and surrounding molecules. We will not consider situations in which the particle density is large enough that interactions between particles are significant.

The momentum exchange between particle and air molecule in a given collision is such a small fraction of the particle momentum that the particle trajectory through phase space can be described as a continuous process using the Fokker-Planck formalism. In the present case, the collision cross section is independent of velocity and both the collisions and medium are isotropic. This allows us to write the collision operator as $$\left(\frac{df}{dt}\right)_c = -\nabla_v \cdot (Cf) - \frac{D_v}{2} \nabla_v^2 f, \quad (13)$$

where the vector C is the coefficient of convection and the scalar $D_v$ is the coefficient of velocity-space diffusion. Realizing that the net flux in velocity-space must vanish when the particle probability distribution f has equilibrated with the air molecules, and equating the convection term with the drag force, it is possible to express the Fokker-Planck coefficients in terms of the particle mobility μ as $$C = -\frac{v - v_0}{\mu m_p} \quad (14)$$

$$D_v = -\frac{2 k_B T}{\mu m_p^2},$$

where $v_0$ is the velocity of the medium, $k_B$ is the Boltzmann constant, and T is the absolute temperature of the medium.

The fundamental solution to Eq. (13) is generalized to a moving medium as $$f = \left[\frac{m_p}{2\pi k_B T(1 - e^{-t/\tau})}\right]^{3/2} \times \exp\left(\frac{-m_p |v - v_0 - (v_i - v_0)e^{-t/2\tau}|^2}{2 k_B T(1 - e^{-t/\tau})}\right), \quad (15)$$

wherein $$\tau \equiv \frac{\mu m_p}{2} \quad (16)$$

is the time constant for equilibration of the particle kinetic temperature with the air temperature. For a particle with a=100 nm in air at standard temperature and pressure, $\tau \approx 50$ ns.

The Einstein-Smoluchowski equation relates the diffusion constant D to mobility by $$D = \mu k_B T \quad (17)$$

and thus to Dv=−2(kBT)2/(Dm2p)Dv=−2(kBT)2/(Dmp2), demonstrating that diffusion in velocity space and in real space are manifestations of the same underlying phenomenon. In our Monte Carlo model we treat collisions of the particle with air molecules as velocity-space diffusion. A particle's random velocity walk then leads deterministically to a diffusion in real space. In our model based on effective velocities and diffusion constants, collisions are treated directly as a diffusion in real space. Both approaches lead to the same result.

The mobility of a particle in a gas $$\mu = \frac{1 + A\frac{l_g}{a} + Q\frac{l_g}{a}e^{-ba/l_g}}{6\pi \eta a} \quad (18)$$

in terms of the gas viscosity $\eta$ and molecular mean free path $l_g$. The constants A=1.25, Q=0.42, and b=0.87 were obtained empirically and $l_g$=68 nm at standard temperature and pressure. In the large particle limit (a/$l_g \gg$1), the Fuchs expression results in Stokes' Law for the drag force on a particle $$F_d = -6\pi \eta a (v - v_0). \quad (19)$$

Figure 10:
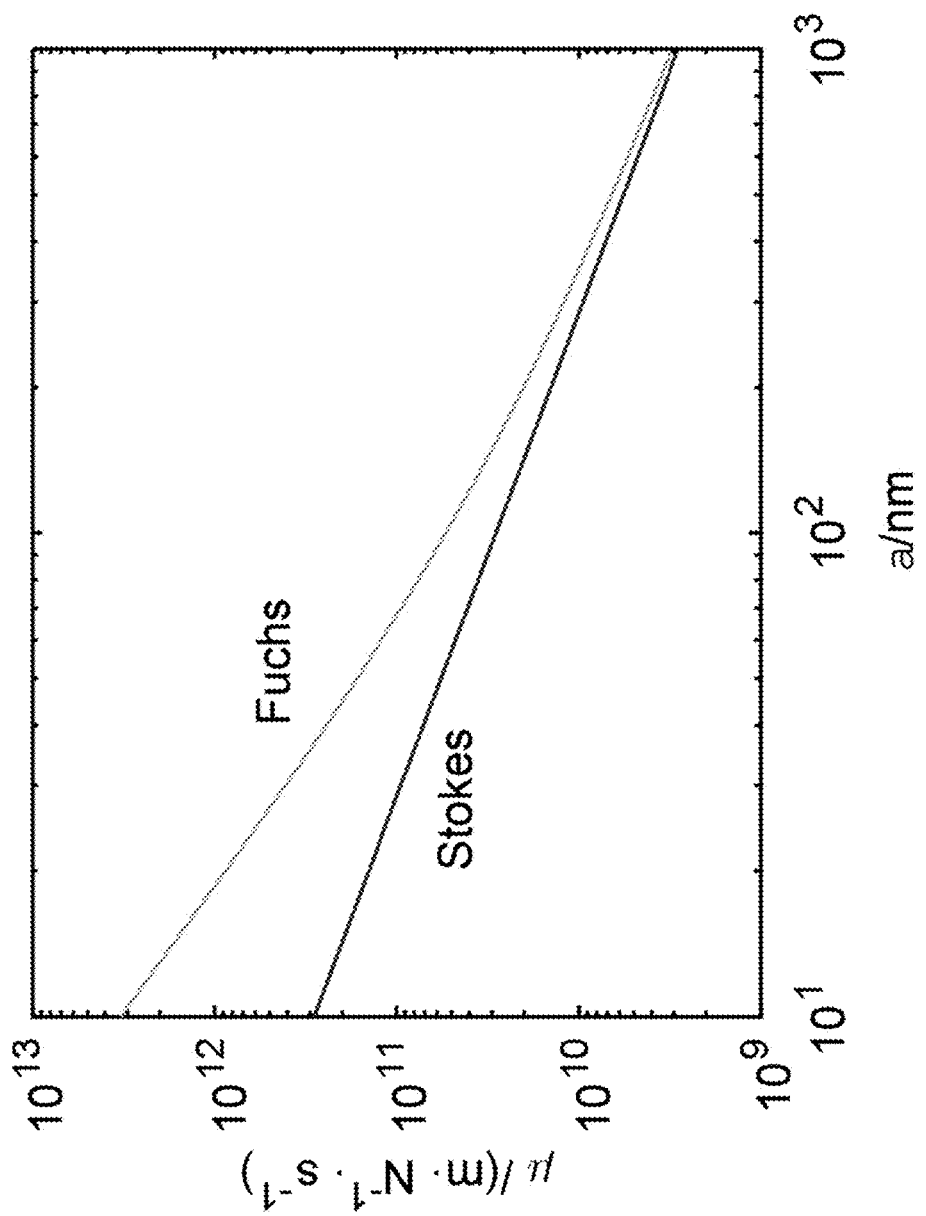
FIG. 10 shows a graph of mobility versus size.

For small particles (a/$l_g$<10), the numerator in the expression above accounts for the transition from fluid to molecular dynamics in which the mobility $\mu$ varies as $a^{-2}$. The Fuchs mobility is compared, in FIG. 10, to mobility in the limit $l_g \to 0$.

With regard to Monte Carlo simulations of particle trajectories, multiplying the Boltzmann equation by wand integrating over all phase-space and multiplying the Boltzmann equation by r and integrating over all phase-space yields the equations of motion for a particle $$\frac{dv_p}{dt} = \frac{F(r,t)}{m_p} + \left(\frac{dv_p}{dt}\right)_c \quad ((20)$$

$$\frac{dr_p}{dt} = v_p \quad ((21)$$

where $$r_p = \int_{-\infty}^{+\infty} r f d^3 v d^3 r$$

$$v_p = \int_{-\infty}^{+\infty} v f d^3 v d^3 r \quad ((22)$$

and the force in the term F(r,t)mpF(r,t)mp is due entirely to optical forces.

The trajectory of a particle is determined numerically from this system of equations using a fourth-order Runge-Kutta discretization method, given an initial velocity and position. The collision term is dealt with by randomly selecting a change in velocity $\Delta v \equiv v_{final} - v_{initial}$ from the time-dependent probability distribution function Eq. (15) given a discrete time interval $\Delta t$. Then $$\left(\frac{dv_p}{dt}\right)_c = \frac{\Delta v}{\Delta t}. \quad (23)$$

The interval $\Delta t$=10 ns was found to achieve satisfactory results. It is much longer than the mean collision time of order 10 fs, yet small enough that a representative particle does not have time to change its position significantly in the external (optical) force field. A particle with radius a=40 nm and moving at thermal velocity moves only about 1 nm in 10 ns. Larger particles move even shorter distances.

Although numerically intensive, the Monte Carlo approach is fully three-dimensional and can easily accommodate an arbitrary optical field and other forces.

With regard to particle trajectories using effective velocities and diffusion constants, an alternate approach to calculating particle trajectories involves working on two length scales: (a) the submicrometer length scale of an individual optical fringe, and (b) the millimeter length scale of the system as a whole. We solve the Fokker-Planck equation for the spatial probability distribution (in contrast to the velocity-space probability distribution in the previous section) of a particle as a function of time in a 1D optical interference pattern. By considering the time-evolution of the probability distribution of a particle, it is possible to find an effective velocity and effective spatial diffusion constant in a regime in which the position and second moment both change linearly in time. After crossing a fringe, the particle finds itself facing a symmetry-equivalent optical landscape, so the macroscopic motion of the particle can be defined by the microscopic constants. Integration of these constants through the experimental setup leads to predictions which are comparable to the Monte Carlo results. Software for this section is available.

Here, we consider the Fokker-Planck equation in a plane wave basis. The mathematical content of the "slowly varying" assumption is that we model the mean motion and its variance in one dimension and that we neglect the small forces in the $\hat{x}$ direction. Because the particle is large compared to the air molecules, it undergoes overdamped Brownian motion and satisfies the Fokker-Planck equation $$\frac{\partial f(z,t)}{\partial t} = D\frac{\partial^2 f(z,t)}{\partial z^2} - \mu \frac{\partial}{\partial z}[F(z)f(z,t)]. \quad (24)$$

The diffusion constant D of the particle is tied to the mobility $\mu$ by Eq. (17), F(z) is the static force on the particle, and f(z, t) is the probability distribution for the location of a particle at time t. (It is the 1D analogue of the distribution used in the previous section, integrated over all velocity space.) Unlike the previous section, here we assume that the particle achieves thermal equilibrium before it moves a significant distance. Physically, f represents a localized function. However, we describe it as an artificially periodic function for mathematical convenience, with the artificial period chosen to be larger than the extent of f.

Since the external force is smooth and periodic, we anticipate a rapidly converging expansion for the probability distribution f(z, t) in a Fourier basis:

$$f(z, t) = \frac{1}{N\Lambda} \sum_{n=-\infty}^{\infty} C_n(t) e^{inkz}, \quad (25)$$

where $\Lambda = \lambda_0/2$, the $c_n(t)$ are complex expansion coefficients, and $k = 2\pi/(N\Lambda)$, where N is the number of interference fringes between the artificial periodic replicas of the solution. Because f(z, t) is real, $c-n=c*nc-n=cn*$. Moreover, the probability normalization is constant in time, i.e., $$1 = \int_{-N\Lambda/2}^{N\Lambda/2} dz f(z, t), \quad (26)$$

which implies $c_0=1$. Putting these facts together, $$f(z, t) = \frac{1}{N\Lambda} \left( 1 + 2\mathrm{Re} \sum_{n=1}^{\infty} C_n(t) e^{inkz} \right). \quad (27)$$

We consider the case of a standing wave optical field and a convective background with the form $$F(z) = F_0 + F_1 \sin(2\pi z/\Lambda), \quad (28)$$

Where $F_1$ is the optical force from Eq. (9). The influence of the background fluid with velocity $v_0$ is implemented by setting the spatially invariant force term to $F_0 = v_0/\mu$ using Eq. (18). Substituting Eq. (25) and Eq. (28) into the partial differential Eq. (24) leads to the system of ordinary differential equations $$\frac{d}{dt} C_n(t) = -Dn^2 k^2 c_n(t) + i v_0 nk c_n(t) - \frac{\mu}{2} F_1 nk c_{n-N}(t) + \frac{\mu}{2} F_1 nk c_{n+N}(t). \quad (29)$$

The relation $c-n=c*nc-n=cn*$ means that it is sufficient to solve only for n>0. Terms with n<0 may be eliminated from the equation in favor of terms with positive n. In the special case $v_0=0$, the solution is symmetric and the cn are real. Moreover, the sum is truncated after a finite number of terms $N_{term}$, i.e., we assume $c_n=0$ for $n>N_{term}$. These relations suffice to limit the number of $c_n$ which need to be found to $N_{term}$. Because F(z) has period $\Lambda$, by Bloch's theorem the system Eq. (29) splits into N independent sets of coupled equations. Furthermore, each independent system of equations is tri-diagonal. The net result is that the computational burden is very low, with a few seconds involved to solve the equations in a particular case.

Figure 11:
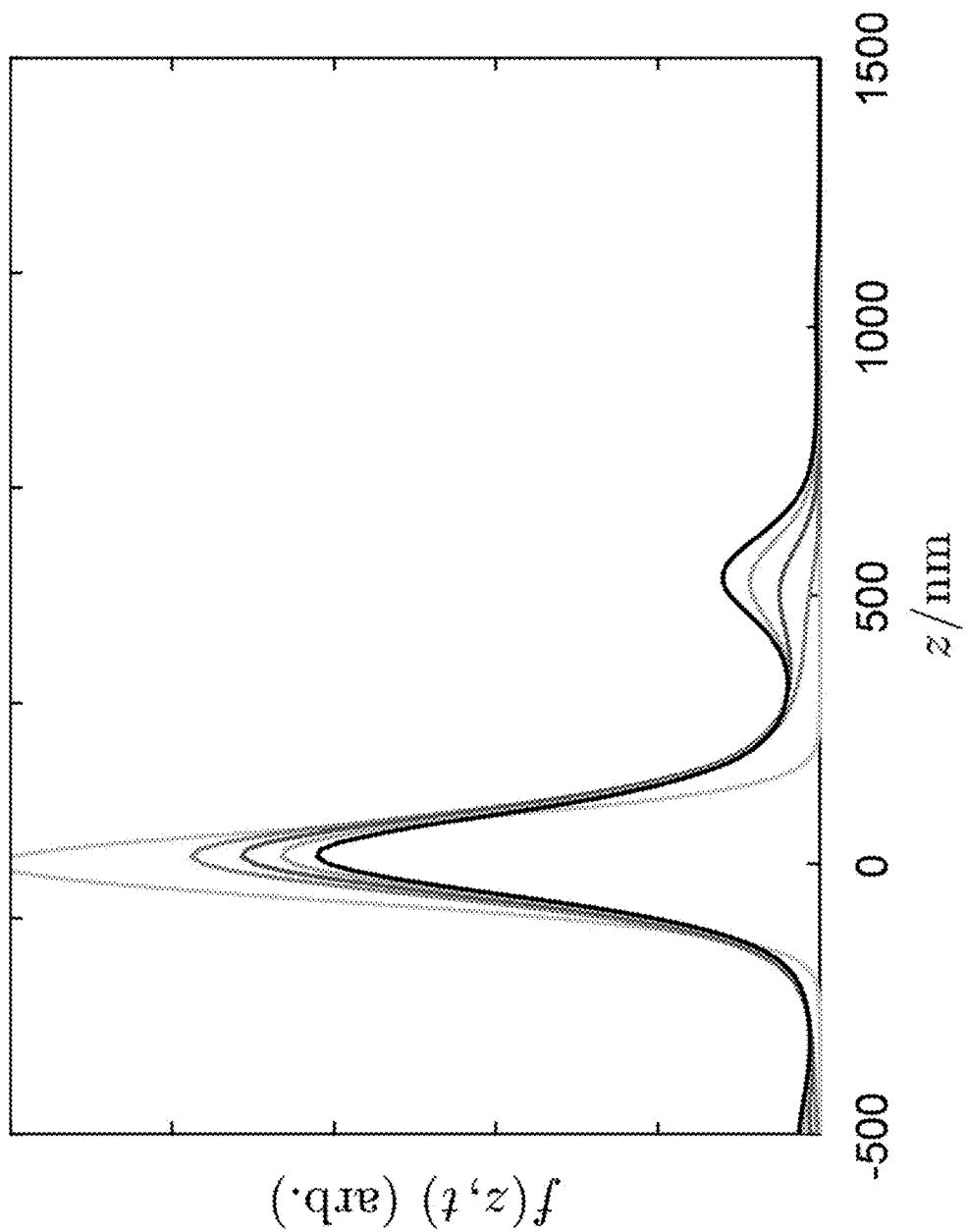
FIG. 11 shows a graph of $f(z,t)$ versus z for solutions of the Fokker-Planck equation.

A typical solution to the Fokker-Planck equation is shown in FIG. 11. An initial Gaussian quickly relaxes within its well, shown by the shift between the blue and green curves, and then more slowly populates the first well downwind as the central well is depopulated. A very small population of the first well upwind is also visible.

Here, we consider analytic limits and program tests. The Fokker-Planck equation has certain recognizable limiting cases. If D=0 and $F_1=0$, Eq. (24) reduces to the advection equation (a one-way wave equation). If F(z)=0, we obtain the diffusion equation at zero velocity and the drift-diffusion equation at finite velocity. The cases of neglecting diffusion and of neglecting drift are considered below. Setting any one parameter among D, $v_0$, and $F_1$ to zero leads to an analytic result for Eq. (29). We verified all three cases numerically for Gaussian starting distributions.

Here, we consider extraction of effective velocities and diffusion constants to obtain two functions $v_{eff}$ and $D_{eff}$ characterizing the linear increase in the mean and variance rate of f(z, t) as a function of particle diameter and field intensity. The system of differential equations is started with a Gaussian distribution of width $\sigma = \Lambda/8$ centered in one of the wells. The times need to be large enough so that there is intra-well equilibration. Numerically converged results are achieved with the parameters in Table 2, which lists parameters used for converged solution of Eq. (29), wherein small a means 40 nm≤a≤110 nm; medium a means 120 nm≤a≤170 nm; large a means 180 nm≤a≤300 nm.

TABLE 2

| Parameter | Small a | Medium a | Large a | Unit | Remark |
| --- | --- | --- | --- | --- | --- |
| N | 32 | 32 | 32 | — | |
| $\Lambda$ | 532 | 532 | 532 | nm | $\lambda_0/2$ |
| $\Delta t$ | 0.5 | 1 | 4 | μs | |
| $N_{step}$ | 512 | 512 | 1024 | — | |
| $N_{term}$ | 512 | 512 | 256 | — | |

Figure 12:
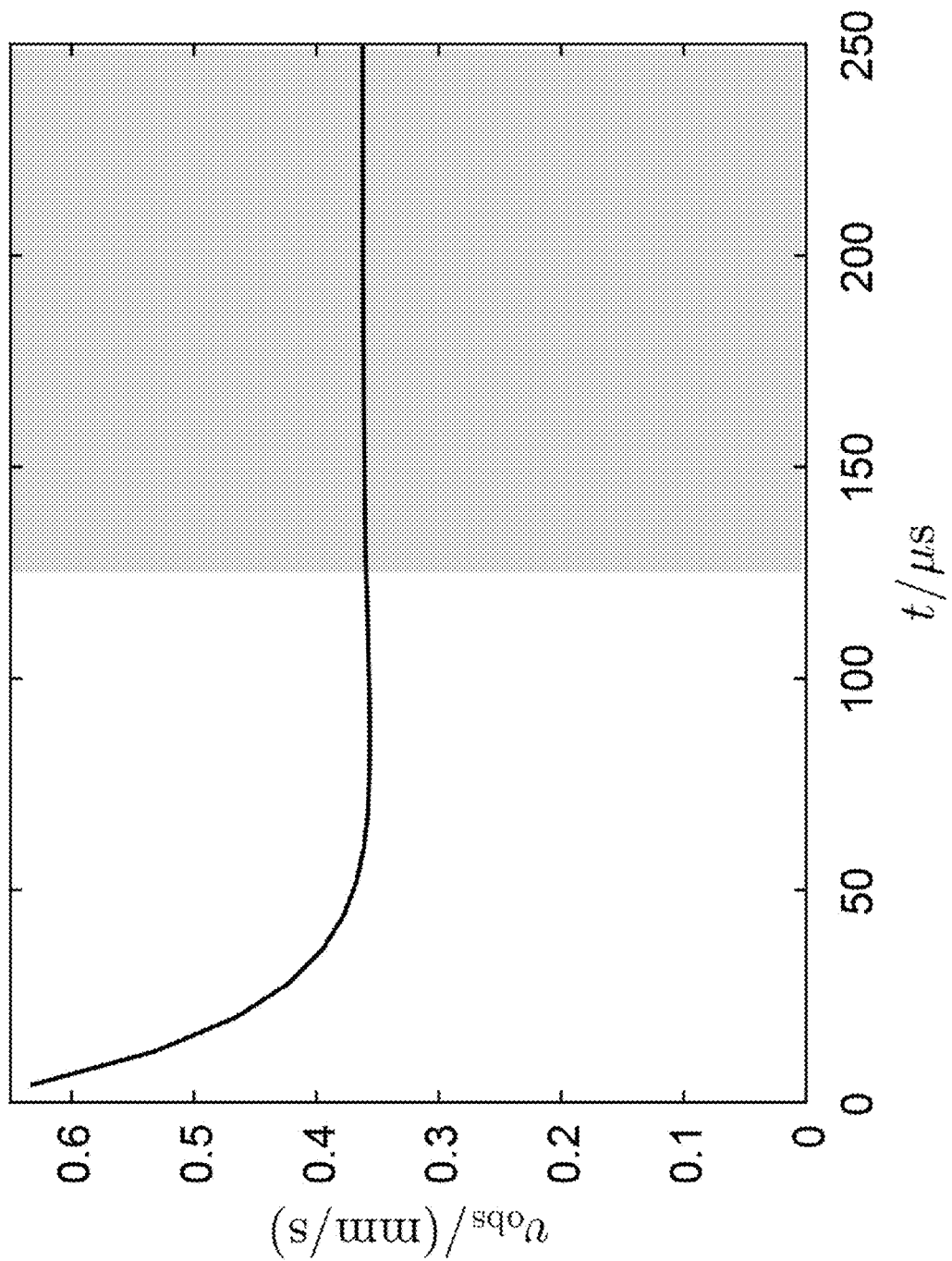
FIG. 12 shows a graph of velocity versus time.

The mean and variance are calculated as a function of time and locally fit to a linear function. The parameters of Table 2 were chosen so that the results yield nearly constant values for $v_{eff}$ and $D_{eff}$ in the second half (in time) of the simulation after the intra-well equilibration. Typical results are shown in FIG. 12 for the solution corresponding to FIG. 11.

Figure 13:
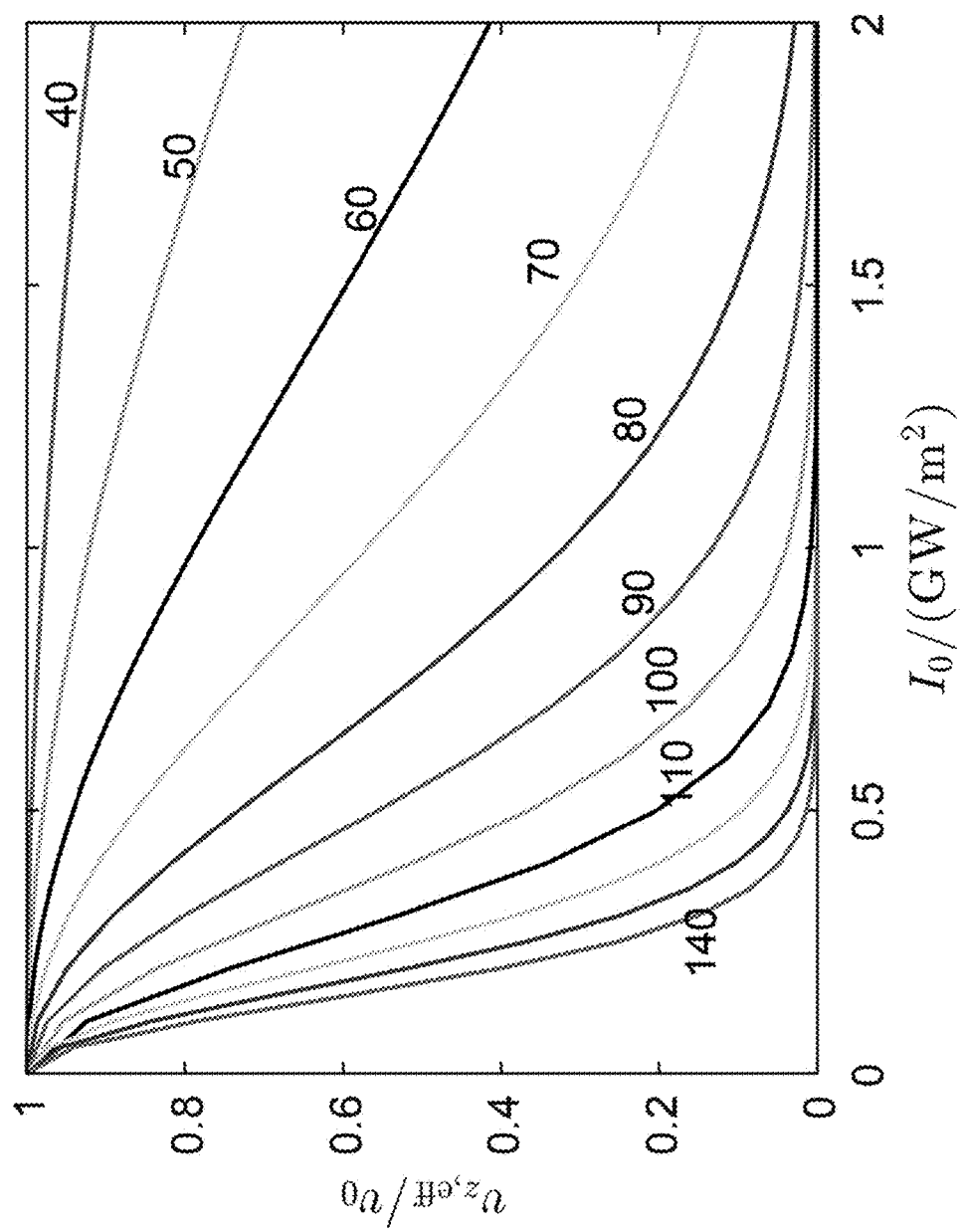
FIG. 13 shows a graph of velocity versus optical intensity.

Effective velocities for several particle radii from 40 nm to 140 nm are shown in FIG. 13. They have been normalized to the velocity at zero optical force. Small particles are relatively unaffected by the optical field, but the effect grows with particle radius. The differences in these effective velocities permit optical sorting, as we see below.

With respect to use of effective constants of motion, the effective velocities and effective diffusion constants could be used as input to Monte Carlo modeling where the steps need to be small compared to changes in the fringe-averaged optical intensity which is typically 1 mm. By comparison, a direct application of Monte Carlo to the drift-diffusion equation requires steps which are small compared to $\Lambda$, equal to 532 nm in our example.

However, the simplicity of the geometry allows a more direct approach. We take the x-component of velocity to be a constant $v_x = v_0 \sin \theta$ with $\theta$ shown in FIG. 8. We will also use $v_z = v_0 \cos \theta$. Because the system is translationally invariant in z, the z motion does not affect the accumulation of either displacement or variance in z position. In the y direction, we need to make an additional physical assumption that the total diffusion in y is small compared to the scale length of the optical field. We test this assumption at the end.

The mean displacement in z compared to displacement without an optical field is given by $$z_1 = \int_{t_0}^{t_1} dt \{ v_{z,eff}[x(t)] - v_{z,0} \} \quad (30)$$

$$= \frac{1}{v_x} \int_{x_0}^{x_1} dx \{ v_{z,eff}(x) - v_{z,0} \}$$

where a particle starts at position $(x_0, 0, z_0)$ and ends at $(x_1, 0, z_1)$, making use of the uniform motion in x. We use the subscript "eff" to denote an average over multiple fringes of the optical field. The variance in $z_1$ ($\sigma 2z\sigma z2$) has two contributions. First, we have the effect of 1 dimensional diffusion in z during the mean crossing time. This is given by $$[\sigma_z^{(D)}]^2 = \frac{2}{v_x} \int_{x_0}^{x_1} dx D_{\mathit{eff}}(x). \quad (31)$$

The contributions to Eqs. (30) and (31) come from different regions. For the velocity integration, the differences in the central region drive the whole phenomenon. For the diffusion integration, since most of the path is through a relatively less intense field, and since the results add in quadrature, the reduction (or even a small increase) in the effective diffusion constant at high intensity has only a few percent effect on the result compared to simply using the zero-field value for the duration of the transit.

A second contribution to σ2zσz2 arises from the variations in crossing times. After the time $t_1 = (x_1 - x_0)/v_x$, the distribution of particles acquires a variance in x given by σ2x=2Dt1σx2=2Dt1. Neglecting a term of order $\sigma_x/(x_1-x_0)$ throughout this argument, the standard deviation in the crossing times is given by $\sigma_t = \sigma_x/v_x$. The drift in z acquires a corresponding standard deviation $$\sigma_z^{(0)} = (v_{2,\mathit{eff}})\sigma_1, \quad (32)$$

where the average is the integral in Eq. (30). These two processes—1D diffusion and variable time to drift—are independent, so the total variance in x is given by $$\sigma_z^2 = [\sigma_z^{(0)}]^2 + [\sigma_z^{(0)}]^2. \quad (33)$$

The variance of position in the y direction is given by the diffusion constant times the crossing time; symbolically, $$\sigma_y^2 = 2D \frac{x_1 - x_0}{v_x}. \quad (34)$$

If we pick the highest value of D used in this study, namely $2.2 \times 10^{-10}$ m$^2$/s, picking the parameters from Table 2 yields $\sigma_y = 43$ μm which is small compared to the beam waist. This justifies the assumption that the diffusion in y may be neglected. Methods of tracking nanoparticles optically has been reviewed recently. It is possible in principle to observe $v_{\mathit{eff}}$ and $D_{\mathit{eff}}$ directly by optical means.

We show optical sorting of aerosol particles by simulating conditions readily implemented in an actual device. Table 3 gives numerical values for simulated parameters. High-power frequency-stabilized lasers with wavelength $\lambda_0$=1064 nm are commonly available. A Fabry-Perot cavity of modest finesse (≈1000) and small numerical aperture (≈$10^{-3}$) can be used to establish a standing wave with intensities great enough to achieve the same magnitude of forces commonly used in optical tweezers. The larger beam waist of the present approach requires more power than optical tweezers, but it renders diffusive transport in y irrelevant and makes a high throughput possible.

TABLE 3

| Parameter | Symbol | Value | Units |
|---|---|---|---|
| Optical wavelength | $\lambda_0$ | 1064 | nm |
| Beam waist radius | $w_0$ | 500 | μm |
| Particle index of refraction | $n_p$ | 1.57 | — |
| Air speed | v | 1 | mm/s |
| Air viscosity | η | 18.6 | $\mu Ns/m^2$ |
| Air temperature | T | 298 | K |
| Bounds of travel in x | $x_0$, $x_1$ | ±1.5 | mm |
| Angle between flow and z-axis | θ | 45 | degrees |

We assume spherical particles of polystyrene, with a real index of refraction $n_p$=1.57. There is no optical absorption by the particles and we do not consider interactions between the particles. The small spatial scale and low flow rate considered ensure laminar flow with Reynolds number Re≈0.2.

The particles are entrained in the 1 mm/s laminar flow of air at standard temperature and pressure from a point source. Although an experimental implementation would utilize a finite diameter particle source instead of a point source, predictions for the former can be estimated by convolving our results over any size input aperture. In doing so, it should be remembered that the flux density from an aperture will be concentrated in the center of the aperture with a parabolic profile because the flow velocity vanishes at the edge of the aperture. The release point is x1=−3 $w_0$. The air velocity vector is in the x−z plane and oriented at 45° to the optical axis.

FIG. 14 shows mean trajectories, from the Monte Carlo model, for several populations of particles characterized by radii from 40 nm to 110 nm travelling across an optical field with $I_0$=2 $GW/m^2$. These simulated trajectories reflect what is shown schematically in FIG. 8, with the dispersion of different particle sizes along the z coordinate in the output plane. The smallest particles travel in nearly a straight line across the optical field, intersecting the output plane near $z_1$=0. Larger particles are deflected by the optical field and intersect the output plane at negative values of $z_1$. All particle trajectories have been projected onto the x−z plane in this figure, but the simulation was fully three-dimensional.

FIG. 15 shows, for the same data, spatial distributions of the particle populations in the output plane. The solid lines are Gaussian fits and provide a reasonably accurate, though not detailed, description of the distributions. This simulation included 1600 individual particles of each size. It follows from FIG. 15 that a continuous uniform distribution of particle sizes going into the sorter will produce a continuous distribution in the output plane. Any given point, or interval, in the output plane corresponds to a distribution of particle sizes whose mean value is a function of z. The width of each size distribution is also a function of z and is about 10 nm (FWHM≈2$\sigma_a$) for radii near a=70 nm.

Table 4 shows a comparison of our two methods for calculating particle trajectories. Here, we compare the positions and one standard deviation widths of the distributions shown in FIG. 15 (Monte Carlo) with the corresponding values obtained from the effective velocity method.

TABLE 4

| a/nm | $z_1$ | $\sigma_z$ |
|---|---|---|
| 40 | 1.12 | 1.01 |
| 50 | 1.11 | 0.98 |
| 60 | 1.05 | 1.00 |
| 70 | 1.02 | 1.04 |
| 80 | 1.01 | 1.04 |
| 90 | 1.01 | 1.08 |

TABLE 4-continued

| a/nm | $z_1$ | $\sigma_z$ |
|------|-------|------------|
| 100  | 1.01  | 1.05       |
| 110  | 1.00  | 1.03       |

Table 4 provides ratios of results from the Monte Carlo model divided by results from the effective constants of motion model for $I_0=2.0$ GW/m².

Figure 16:
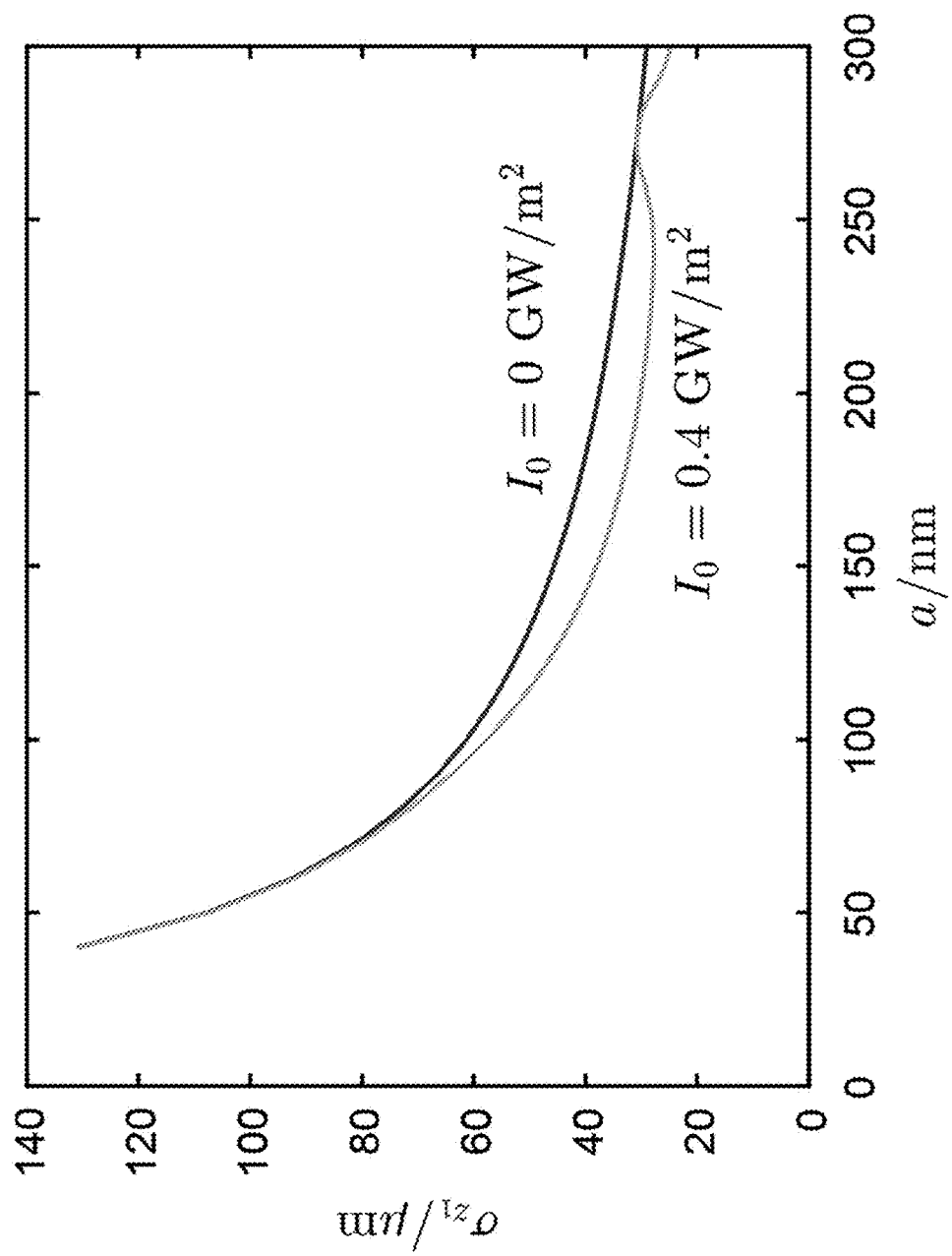
FIG. 16 shows a graph of standard deviation versus size.

The widths of the spatial distributions are determined by diffusion during the time the particles transit the optical field from the point source to the output plane. Although the optical field suppresses diffusion for some part of that transit time, depending on particle size, this suppression is not very important in determining distribution widths. Most of the diffusive expansion of the particle stream occurs immediately after release from the point source because diffusive expansion is proportional to $t^{1/2}$. FIG. 16 compares the distribution widths in the output plane for $I_0=0.4$ GW/m² with those obtained when no optical field is present ($I_0=0$). The difference in distribution width at the output is due almost entirely to the difference in particle size.

Figure 17:
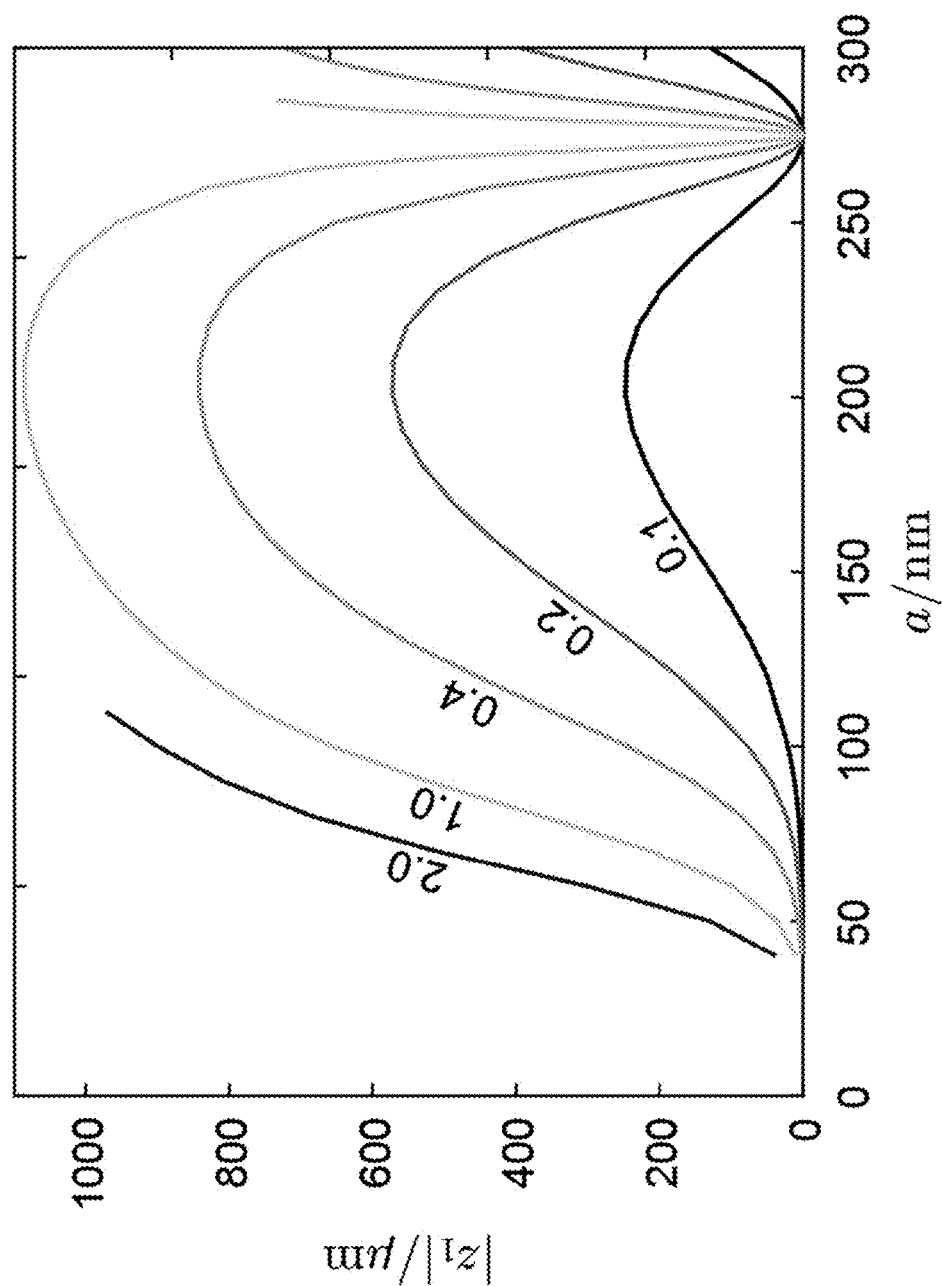
FIG. 17 shows a graph of position Z1 versus radius.

We use the effective constants of motion approach to explore particle sorting over a larger range of particle sizes and a range of optical intensities. First, we look at the mean deflection $z_1$ of particles in the output plane as the result of interaction with the optical field. FIG. 17 gives $|z_1|$ as a function of particle radius for a number of values of $I_0$. (All values of $z_1$ are negative or zero.) In general, the deflection increases like the absolute magnitude of the force (FIG. 9), though the increase is not linear with either radius or intensity. The radius a=275 nm corresponds to the first zero-crossing of the force (FIG. 9). The deflection also vanishes here, but unlike the force, it does not reverse sign for larger a. The function of the standing wave in this sorting configuration is simply to provide a barrier to particle movement along z and a reversal in the sign of the force simply corresponds to a change of $\pi$ in the phase of the fringes, but the nature of the barrier remains essentially the same. Thus, as a increases toward the zero-crossing, deflection decreases. It vanishes at the zero-crossing, but then increases again as the magnitude of the force increases with further increases in a.

Figure 14:
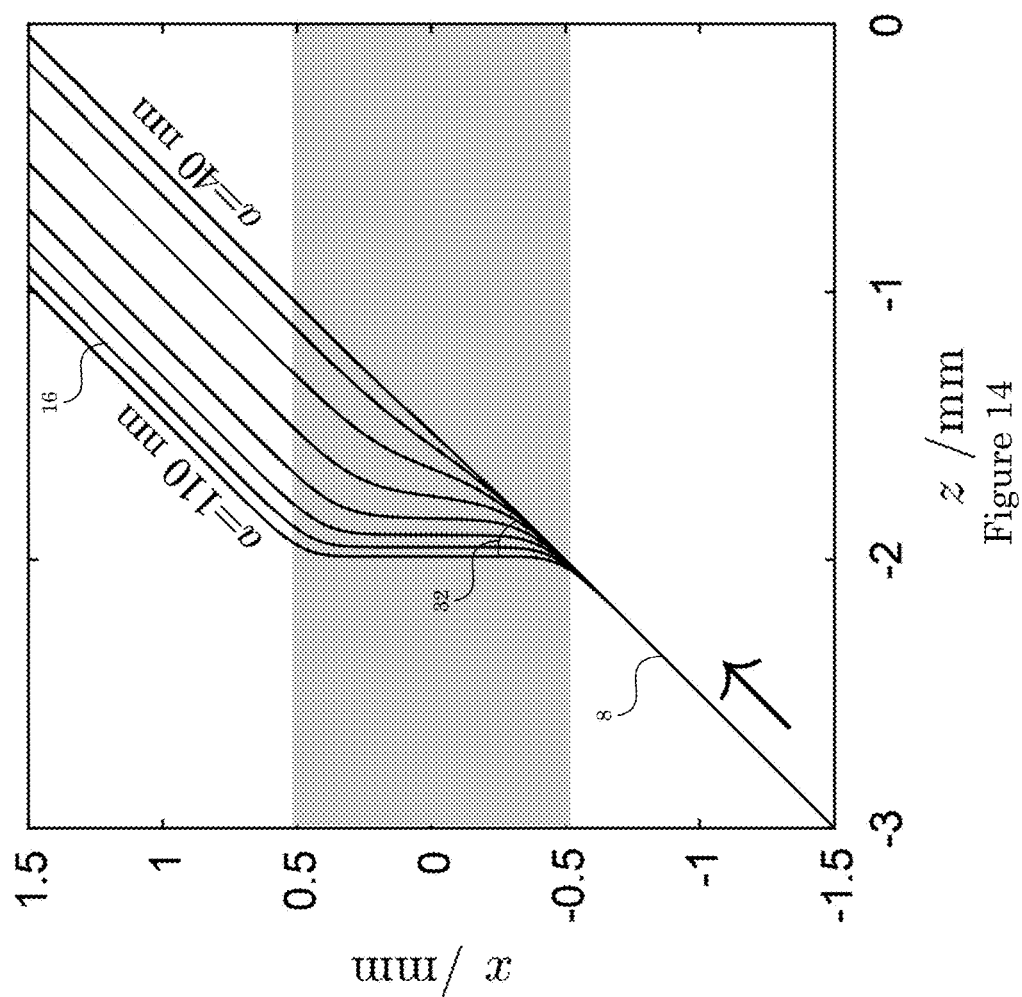
FIG. 14 shows a graph of position X versus position Z.

The vanishing of the optical force imposed by a standing wave on particles of certain sizes is known, but its potential exploitation for determination of absolute particle sizes has not been realized. Particles with radii corresponding to the zero-crossings exit the optical field at the edge of the sorted particle stream with both larger and smaller particles deflected to the left in FIG. 14. This enables an easy identification of the desired particles because one need only find the edge of the sorted stream, instead of an absolute position. The radius corresponding to the zero-crossing is a function only of the wavelength of the optical field and the index of refraction of the particle (and the medium when it differs from unity). The wavelength can be adjusted to nearly any desired value and measured absolutely to any practically useful precision by common methods. The index of refraction can also be determined by other well-known means, although not with the same level of precision. Nevertheless, the precision is likely good enough to obtain particle size values to better than 0.1% absolute accuracy.

The dispersion of particle sizes along the output plane is the derivative $dz_1/da$ of the deflection. In FIG. 17, one can see ranges of particle radius that are potentially most attractive for sorting particles by size. The Rayleigh regime is one such region, using relatively large intensities. Even better are the regions on either side of the zero-crossing (a=275 nm) where the deflection is the most sensitive to particle radius. The neighborhood of maximum deflection (a=205 nm), on the other hand, is less desirable for sorting. Although the deflection is large, a wide range of particle sizes end up at the same position in the output plane.

More generally, values of a for which the force has an extremum or a zero-crossing also correspond to zero dispersion. There are two such values for the range covered in FIG. 17, but there are many more such values as a increases because the force continues to alternate between positive and negative values. Although zero-dispersion is generally to be avoided, these points, particularly the zero-crossing points, offer the possibility of creating bimodal size distributions. For example, an input distribution covering the range a=250 nm to a=300 nm, will result in bimodal distributions across the output. At $z_1=29$ µm, the distribution will have modes with mean values a=272 nm and a=278 nm. Unimodal size distributions, including monodisperse distributions, can be created by utilizing regions of the deflection curve farther from the extrema and zero-crossing points.

Figure 15:
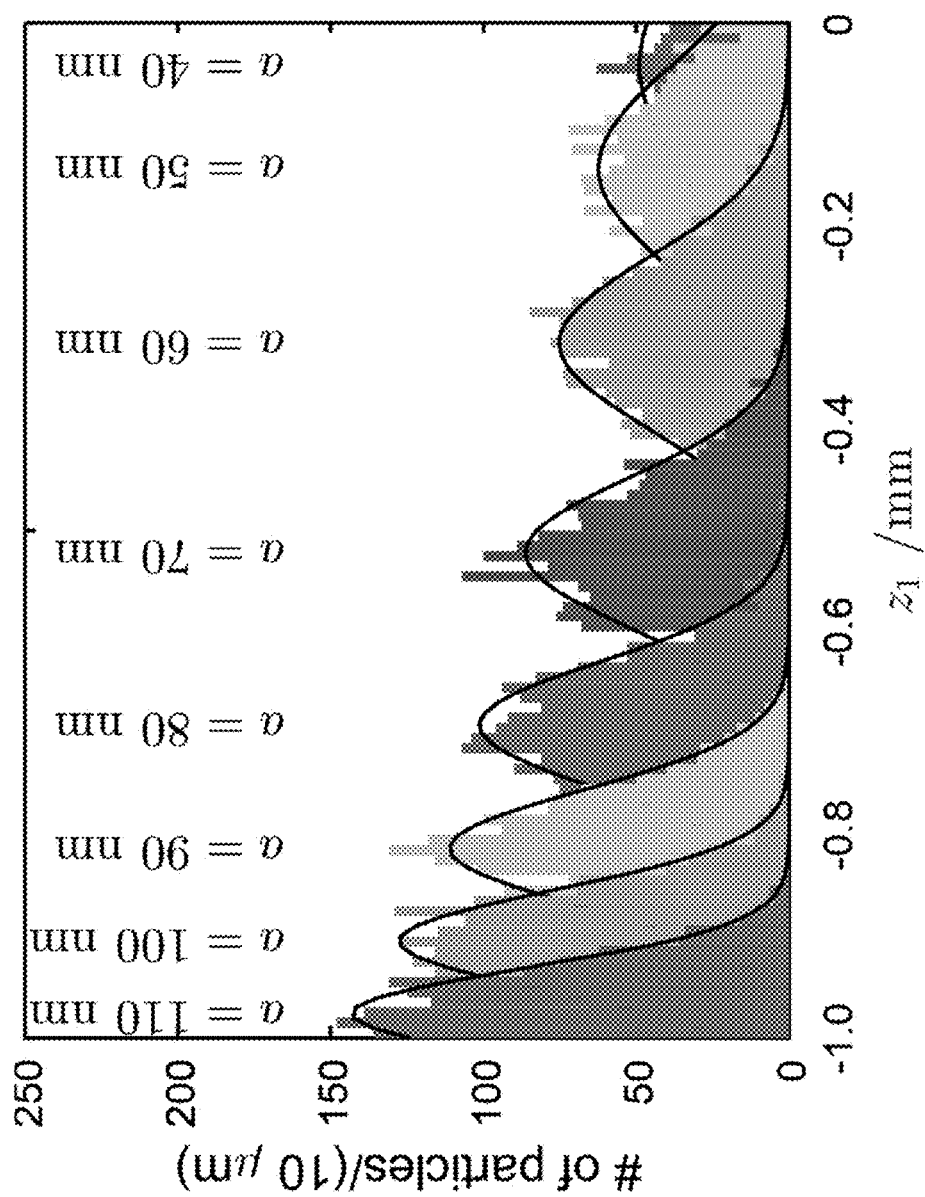
FIG. 15 shows a graph of a number of particles versus position Z1.
Figure 18:
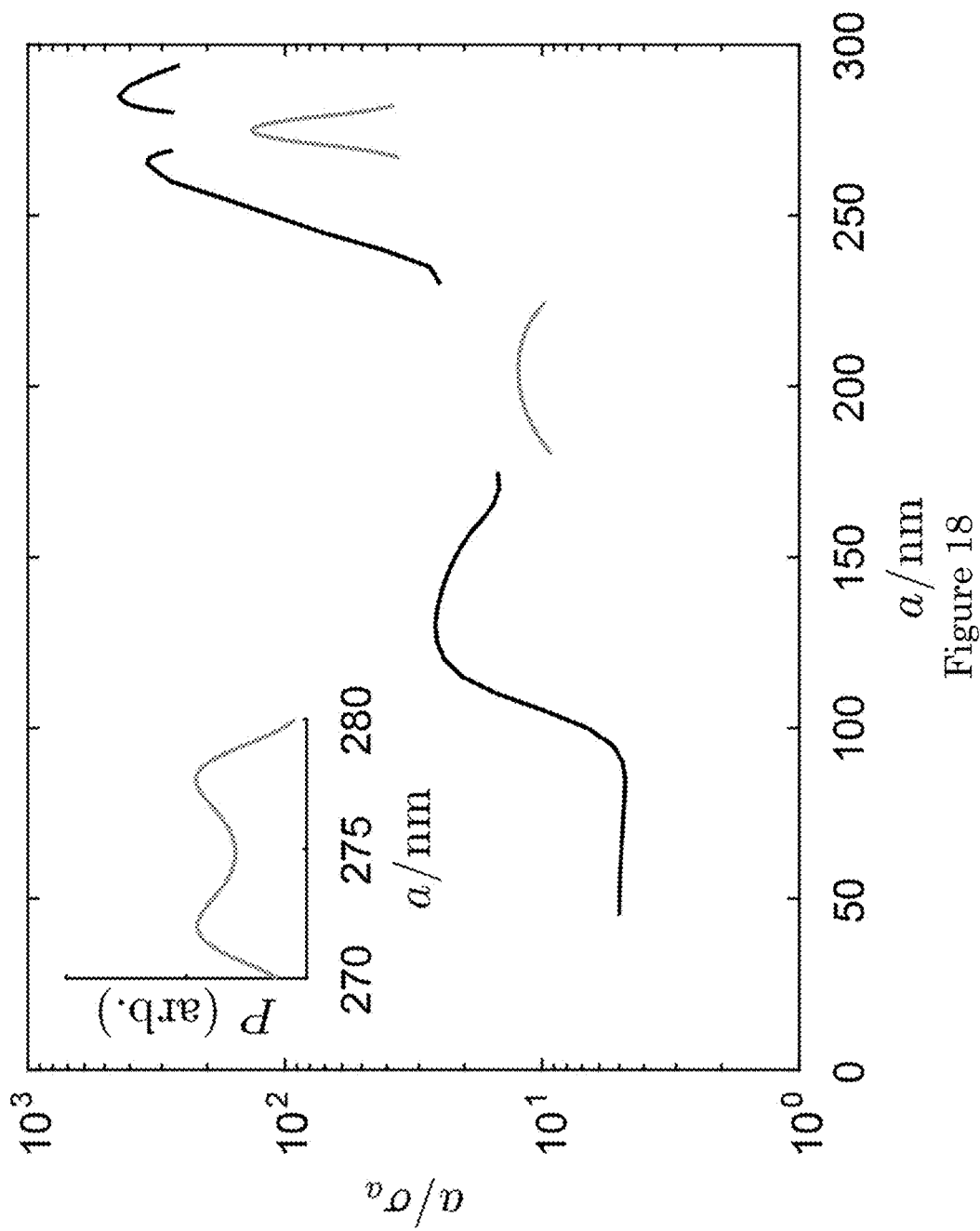
FIG. 18 shows a graph of resolving power versus particle radius.

The sorting resolution depends on, in addition to dispersion $dz_1/da$, the width of the spatial distributions created by each particle size, the distributions illustrated in FIG. 15. More specifically, the resolution is the standard deviation $\sigma_a$ of the size distribution as a function of particle radius (as opposed to position) at a given location in the output plane. Resolution has the units of length. In addition, we define resolving power R as the ratio $$R \equiv \frac{a}{\sigma_a}, \quad (35)$$

where $\sigma_a$ and a are the standard deviation and mean of the relevant size distribution. The resolving power as a function of particle radius for $I_0=0.4$ GW/m² is shown in FIG. 18. Resolving powers larger than 100 are indicated in regions near the zero-crossing point. There are much wider ranges of particle size for which the resolving power exceeds 10. In these regions, resolving powers in excess of 100 can be obtained by combining two sorting stages in series. A resolving power of 100 is sufficient for many applications. Similar resolving power has been reported for an array of optical tweezers.

We have discussed the deflection and resolving power as though the features in those curves are fixed with respect to particle size. In fact, high resolving power regions can be shifted relative to particle size by changing the optical wavelength. This allows for considerable flexibility in creating and measuring size distributions.

Finally, we consider particle throughput. There are two factors affecting throughput that are relevant to this specific geometry for sorting particles. One is perturbation of the optical field by the particles being sorted and another is the maximum flux of particles that can be put through a point-like source.

We imagine obtaining a standing wave of sufficient intensity inside of a resonant optical cavity. The power loss from the cavity by scattering from particles must be small compared to mirror loss so that the power in the cavity is not dependent on the number of particles. Power loss in an empty cavity is $P_c(1-R)$ where $P_c$ is the circulating power and R is the mirror reflectivity. Power loss by optical scattering from N particles with scattering cross section $\sigma$ is $$P_s = IN\sigma. \quad (36)$$

Assuming a Gaussian mode with beam waist $w_0$ and particles distributed uniformly across the beam between $x=-2--\sqrt{}w0x=-2w0$ and $x=+2--\sqrt{}w0x=+2w0$, $$P_s = \frac{N\sigma}{2\sqrt{\pi}\,w_0^2}P_c \qquad (37)$$

where we have used erf(2)≈1. Making scattering losses negligible in comparison to mirror losses, gives the constraint $$N \ll 2\sqrt{\pi}\,w_0^2\frac{1-R}{\sigma}. \qquad (38)$$

Particle throughput Γ is the product of N and the velocity Vc/2--≈Vc/2 across the optical field divided by the distance, which we have taken as 22--≈w022w0. Thus, $$\Gamma \ll \frac{\sqrt{\pi}}{2}w_0\frac{1-R}{\sigma}V_c. \qquad (39)$$

Using the values R=0.999, a=50 nm giving $\sigma=1.7\times10^{-17}$ m$^2$, $V_c=1\times10^{-3}$ m/s, and $w_0=0.5$ mm gives the constraint $\Gamma \ll 3\times10^7$ s$^{-1}$.

Commercially-available aerosol generators are generally limited to particle densities of $10^{14}$ m$^{-3}$. This limits the flux of particles that can be generated by a source of finite size. Considering a tube source with cross-sectional radius r=18 μm and a cross-sectionally averaged flow velocity of 1 mm/s, the corresponding flux is F=$10^2$ s$^{-1}$. This is not a fundamental limit as there are a number of changes that can be made to increase this limit. Particle sources, as many as 100, can be placed in parallel along the length of a cavity, as long as sufficient separation is maintained. The finesse of the cavity can be increased by an order of magnitude, allowing the flow velocity and flux to be increased proportionally. It may also be possible to increase the particle density, by as much as an order of magnitude, for the short times during which the particles are being sorted.

It is contemplated that trajectories of aerosol particles in air flowing through an optical field are determined by the interplay of optical forces, convection, and diffusion. The latter two are produced by random collisions of the particles with air molecules. As provided in the Example, we have derived, from first principles, the optical force on spherical dielectric particle of arbitrary radius in a standing wave. For $a/\lambda_0 \to 0$, our evaluation of the Maxwell stress tensor is equivalent to the expression denoted as the gradient force by others. For larger radii, the force alternates between positive and negative values with decreasing amplitude, a result that has been observed previously.

We have evaluated collisional forces using two distinct approaches, implemented in isolation from each other, in order to validate our results. The first method integrates the microscopic equations of motion to determine individual particle trajectories for large populations of particles. Brownian motion is incorporated with Monte Carlo methods. The second method solves the macroscopic fluid equations of motion. Computational efficiency is achieved by averaging velocity and the diffusion coefficient over the fine-scale features of the optical field before integrating the macroscopic equations of motion. These methods provide a description of particle trajectories in air flowing through a standing wave Gaussian mode optical field. Moreover, this Example provides an optical scheme for sorting particles with high throughput and high resolution resolving power. This scheme diverges from the paradigm of high numerical aperture optics based on optical tweezers.

With regard to Fokker-Planck equation without diffusion, if we neglect diffusion, or equivalently, consider T=0, we may obtain an analytic result for the effective velocity of a point particle traversing the interference fringe. If we fix the drift velocity $v_0>0$, there is some sufficiently small value of the optical potential $I_0$ for which the optical well no longer traps the particle. In this case, the effect of the optical potential is to modify the average velocity of travel through the potential, but not to bring it to zero. The average is that of a point particle moving through a complete spatial period Λ. We introduce v(z) to be the instantaneous speed at position z. The time $t_1$ to cross an interference fringe is given by $$\begin{aligned} t_1 &= \int_0^\Lambda dz\frac{1}{v(z)} \\ &= \mu^{-1}\int_0^\Lambda dz\left[F_0 + F_1\sin\left(\frac{2\pi z}{\Lambda}\right)\right]^{-1} \\ &= \mu^{-1}\Lambda(F_0^2 - F_1^2)^{-1/2},\quad |F_1|<|F_0|. \end{aligned} \qquad (40)$$

We use Eq. (40) to obtain the effective velocity $$v_{\text{eff}} = \frac{\Lambda}{t_1} = \mu(F_0^2 - F_1^2)^{1/2} = v_0\left(1 - \frac{F_1^2}{F_0^2}\right)^{1/2}. \qquad (41)$$

If there is no optical force, i.e., $F_1=0$, then $v_0=\mu F_0$ is recovered. As the optical force $F_1$ increases, the effect is to reduce the average speed. Ultimately, the average speed falls to zero with a square root singularity as $F_1 \to F_0$ from below. In this limit, the particle is marginally trapped. The greatest sensitivity of the effective velocity $V_{\text{eff}}=\Lambda/t_1$ on small changes in the optical force $F_1$ occurs near marginal trapping. Our program reproduces the analytic result of Eq. (41).

With regard to Fokker-Planck equation without drift, if we have no drift but have diffusion, and consider the limit of large well depth, the transition rate is given by $$\frac{1}{\tau} = \mu M \frac{\omega_A \omega_C}{2\pi}e^{-\Delta U/kT} \qquad (42)$$

where the potential energy surface is given by $$U(z) \approx \frac{M\omega_A^2}{2}(z-z_A)^2 \qquad (43)$$

near the quadratic minimum at $z=z_A$ and $$U(z) \approx \Delta U - \frac{M\omega_C^2}{2}(z-z_C)^2 \qquad (44)$$

near the quadratic maximum at $z=z_C$. The exact form of the potential surface does not enter the quoted result.

For this numerical test, we use Stokes' Law, Eq. (19), and the Rayleigh force law, Eq. (8). The energy of a particle in a light field is given by the integral of the 1D optical force $$U(z) = \frac{4\pi n_2 a^3 I_0}{c} \frac{n_p^2 - 1}{n_p^2 + 2} \cos\left(\frac{2\pi z}{\Lambda}\right). \tag{45}$$

From Eq. (45), we may give the energy difference between the top and the bottom of the well as $$\Delta U = \frac{8\pi n_2 a^3 I_0}{c} \frac{n_p^2 - 1}{n_p^2 + 2}. \tag{46}$$

Similarly, by a second order Taylor expansion of the cosine $$\frac{M\omega_A^2}{2} = \frac{M\omega_C^2}{2} = \frac{M\omega_A\omega_C}{2} = \frac{8\pi^3 n_2 a^3 I_0}{c\Lambda^2} \frac{\varepsilon_p - \varepsilon_m}{\varepsilon_p + 2\varepsilon_m}.$$

Figure 19:
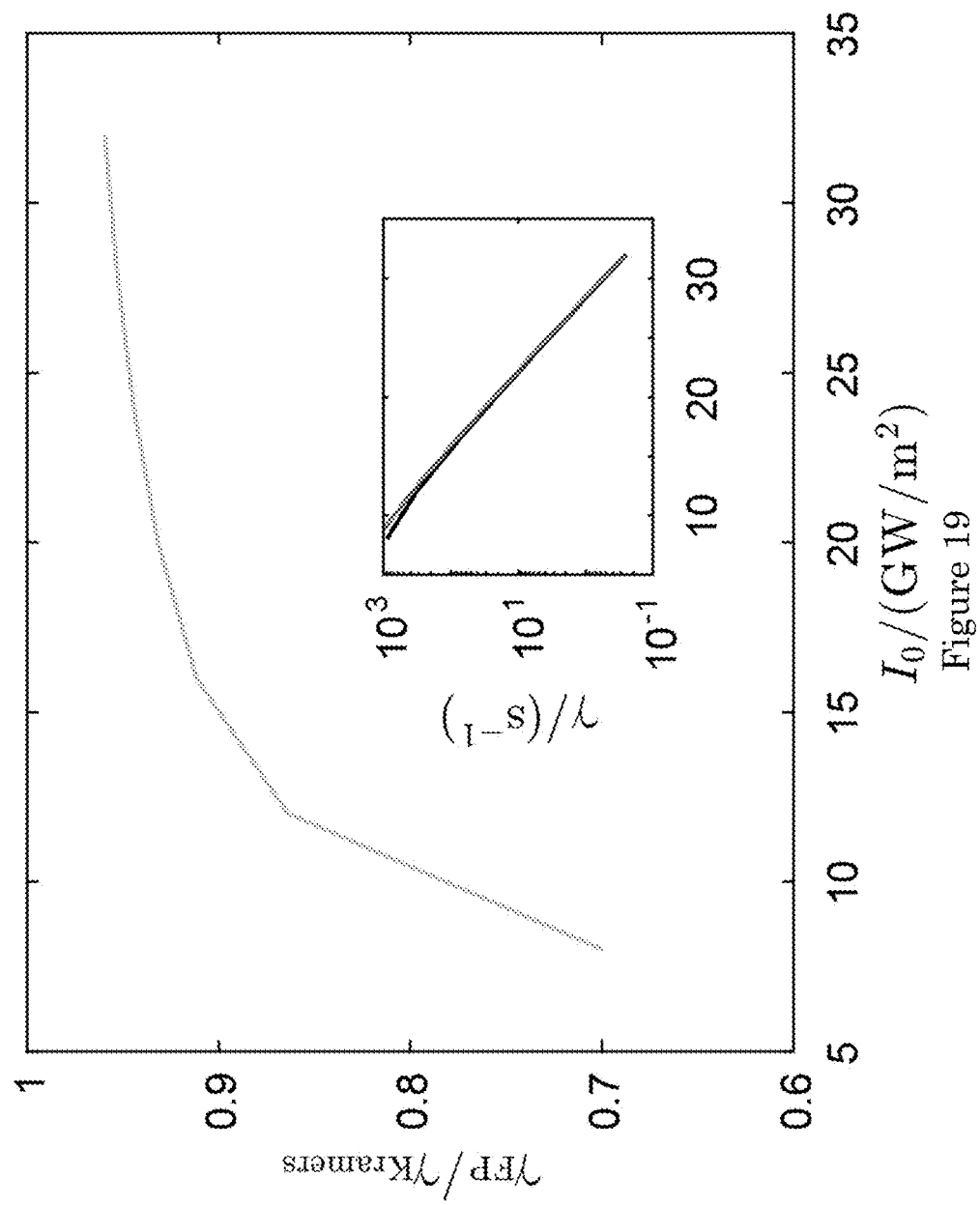
FIG. 19 shows a graph of escape rate versus optical intensity.

As a validity check, we compare our solutions to transition rates of a particle over a barrier due to Brownian motion. To make this comparison, we connect the transition rates to the diffusion constant. The diffusion constant and the effective velocity is $$D_{\text{eff}} = \frac{\Lambda^2}{2}(k_+^{(hop)} + k_-^{(hop)}) \tag{47}$$

and $$v_{\text{eff}} = \Lambda(k_+^{(hop)} - k_-^{(hop)}). \tag{48}$$

where the dimensional constant $\Lambda$ is added here. Eq. (47) may also be obtained by comparing at large times the Gauss-Weierstrass solution to the heat equation for the continuous case to the discrete Poisson distribution arising from hopping. The k(hop)±k±(hop) are the hopping rates with (+) and against (−) the convective current. For simplicity, we confine the check to the case without a convective fluid, i.e., $v_{\text{eff}}=0$ so $k_+^{(hop)}=k_-^{(hop)}$. The transition rates discussed above and the Fokker-Planck equation are shown in FIG. 19. The numerical solution is seen to approach an asymptotic formula for large values of the trapping.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. An optical particle sorter comprising:
   a particle receiver comprising:
      a particle entrance that receives a plurality of particles;
      an optical entrance that receives light and that is geometrically disposed at a non-parallel angle with respect to the particle entrance;
      a sorted particle exit opposing the particle entrance and that communicates sorted particles from an optical interference site; and
      the optical interference site interposed between the particle entrance and the sorted particle exit;
   a first light source in optical communication with the particle receiver and that:
      produces a first light; and
      produces a standing wave optical interference pattern in the optical interference site of the particle receiver; and
   a particle source in fluid communication with the particle receiver and that:
      provides the particles; and
      communicates the particles to the particle receiver at an acute angle with respect to the standing wave optical interference pattern 24,
   wherein the optical particle sorter sorts the particles into a plurality of sorted particles that exit the particle receiver at the sorted particle exit, and the sorted particles propagate in a plurality of deflected paths relative to a path of propagation of the particles at the particle entrance, the deflected path of individual sorted particles based on a sorting parameter comprising a dielectric constant, a magnetic permeability, a particle volume, or a combination comprising at least one of the foregoing sorting parameters of the particles.

2. The optical particle sorter of claim 1, further comprising:
a second light source in optical communication with the particle receiver and that produces a second light,
wherein the second light in combination with the first light form the standing wave optical interference pattern in the optical interference site of the particle receiver.

3. The optical particle sorter of claim 1, further comprising:
a first mirror disposed at the optical entrance; and
a second mirror disposed opposing the first mirror,
wherein the first mirror and the second mirror are arranged as an optical cavity.

4. The optical particle sorter of claim 3, wherein the optical cavity comprises a Fabry Perot cavity.

5. The optical particle sorter of claim 1, wherein the particle source provides a fluid, and the fluid propagates in a plurality of laminar streamlines from the particle source to the particle receiver.

6. The optical particle sorter of claim 5, wherein the particles are disposed in the fluid and propagate along the laminar streamlines of the fluid from the particle source to the particle receiver.

7. The optical particle sorter of claim 1, further comprising:
a collector that comprises a plurality of tubes disposed proximate to the sorted particle exit and distal to the particle entrance,
wherein the plurality of tubes comprises:
a first tube that receives first sorted particles that propagate at a first deflected path; and
a second tube that receives second sorted particles that propagate at a second deflected path.

8. The optical particle sorter of claim 7, wherein the second deflected path is greater than the first deflected path.

9. The optical particle sorter of claim 8, wherein individual second sorted particles have a second particle volume, and individual first sorted particles have a first particle volume that is less than the second particle volume.

10. The optical particle sorter of claim 1, further comprising:
a particle detector that detects the sorted particles.

11. The optical particle sorter of claim 1, wherein the particles comprise a protein.

12. The optical particle sorter of claim 1, wherein a particle volume of the particles is from 1000 cubic nanometers ($nm^3$) to 100 cubic micrometers ($\mu m^3$).

13. A process for optically sorting a plurality of particles, the process comprising:
providing a particle receiver of claim 1;
producing the particles;
receiving the particles by the particle receiver;
receiving the first light by the particle receiver;
producing the standing wave optical interference pattern in the optical interference site of the particle receiver from the first light;
subjecting the particles to an optical gradient force from the standing wave optical interference pattern;
deflecting the particles into the plurality of deflected paths to form the sorted particles from the particles such that the deflected path of individual sorted particles is based on a sorting parameter comprising a dielectric constant, a magnetic permeability, a particle volume, or a combination comprising at least one of the foregoing sorting parameters of the particles; and
propagating the sorted particles from the optical interference site through the deflected paths to the sorted particle exit that opposes the particle entrance to optically sort the particles.

14. The process for optically sorting a plurality of particles of claim 13, further comprising:
providing a second light from a second light source in optical communication with the particle receiver; and
forming the standing wave optical interference pattern by combining the first light and the second light.

15. The process for optically sorting a plurality of particles of claim 13, further comprising:
providing a fluid from the particle source; and
propagating the fluid in a plurality of laminar streamlines from the particle source to the particle receiver.

16. The process for optically sorting a plurality of particles of claim 15, wherein the particles are disposed in the fluid and propagate along the laminar streamlines of the fluid from the particle source to the particle receiver.

17. The process for optically sorting a plurality of particles of claim 13, further comprising:
collecting the particles by a collector comprising a plurality of tubes disposed proximate to the sorted particle exit and distal to the particle entrance,
wherein the plurality of tubes comprises:
a first tube that receives first sorted particles that propagate at a first deflected path; and
a second tube that receives second sorted particles that propagate at a second deflected path.

18. The process for optically sorting a plurality of particles of claim 17, wherein the second deflected path is greater than the first deflected path.

19. The optical particle sorter of claim 18, wherein individual second sorted particles have a second particle volume, and individual first sorted particles have a first particle volume that is less than the second particle volume.

* * * * *